US009131884B2

(12) United States Patent
Holmes et al.

(10) Patent No.: US 9,131,884 B2
(45) Date of Patent: Sep. 15, 2015

(54) MEDICAL DEVICE FOR ANALYTE MONITORING AND DRUG DELIVERY

(75) Inventors: Elizabeth A. Holmes, Palo Alto, CA (US); Shaunak Roy, San Mateo, CA (US); John Howard, Saratoga, CA (US); Chengwang Wang, Mountain View, CA (US)

(73) Assignee: Theranos, Inc., Palo Alto, CA (US)

( * ) Notice: Subject to any disclaimer, the term of this patent is extended or adjusted under 35 U.S.C. 154(b) by 1130 days.

(21) Appl. No.: 13/049,813

(22) Filed: Mar. 16, 2011

(65) Prior Publication Data

US 2011/0166553 A1 Jul. 7, 2011

Related U.S. Application Data

(60) Continuation of application No. 11/202,206, filed on Aug. 12, 2005, now Pat. No. 8,101,402, which is a division of application No. 10/937,872, filed on Sep. 10, 2004, now Pat. No. 7,291,497.

(60) Provisional application No. 60/501,847, filed on Sep. 11, 2003.

(51) Int. Cl.
| | |
|---|---|
| *C12M 1/34* | (2006.01) |
| *A61B 5/1455* | (2006.01) |
| *A61B 5/00* | (2006.01) |
| *A61B 5/15* | (2006.01) |
| *A61B 5/145* | (2006.01) |
| *A61B 5/1473* | (2006.01) |
| *A61B 5/1477* | (2006.01) |
| *A61M 37/00* | (2006.01) |
| *B01L 3/00* | (2006.01) |

(Continued)

(52) U.S. Cl.
CPC ............ *A61B 5/14556* (2013.01); *A61B 5/0024* (2013.01); *A61B 5/0031* (2013.01); *A61B 5/145* (2013.01); *A61B 5/1411* (2013.01); *A61B 5/1455* (2013.01); *A61B 5/1473* (2013.01); *A61B 5/1477* (2013.01); *A61B 5/14514* (2013.01); *A61B 5/14542* (2013.01); *A61B 5/14546* (2013.01); *A61B 5/417* (2013.01); *A61B 5/4839* (2013.01); *A61B 5/685* (2013.01); *A61B 5/6865* (2013.01); *A61M 37/0015* (2013.01); *B01L 3/5027* (2013.01); *A61B 5/1486* (2013.01); *A61B 5/14532* (2013.01); *A61B 2560/0412* (2013.01); *A61M 5/14276* (2013.01); *A61M 2005/14513* (2013.01); *A61M 2005/1726* (2013.01); *A61M 2037/0023* (2013.01); *A61M 2205/0244* (2013.01); *A61M 2205/3569* (2013.01); *A61M 2205/3592* (2013.01); *A61M 2205/50* (2013.01); *B01L 3/502707* (2013.01); *B01L 3/502761* (2013.01); *B01L 3/502776* (2013.01); *B01L 2200/10* (2013.01); *B01L 2300/023* (2013.01); *B01L 2300/024* (2013.01); *B01L 2300/0636* (2013.01); *B01L 2300/0654* (2013.01); *B01L 2300/0816* (2013.01); *B01L 2400/0406* (2013.01); *B01L 2400/0415* (2013.01); *B01L 2400/0472* (2013.01); *B01L 2400/0487* (2013.01); *G01N 2035/00158* (2013.01)

(58) Field of Classification Search
None
See application file for complete search history.

(56) References Cited

U.S. PATENT DOCUMENTS

| | | | |
|---|---|---|---|
| 4,003,379 | A | 1/1977 | Ellinwood |
| 4,146,029 | A | 3/1979 | Ellinwood |

(Continued)

FOREIGN PATENT DOCUMENTS

| | | |
|---|---|---|
| CN | 2559986 | 7/2003 |
| JP | 2003525432 A | 8/2003 |

(Continued)

OTHER PUBLICATIONS

European search report and search opinion dated Mar. 6, 2012 for EP Application No. 10179887.4.

(Continued)

*Primary Examiner* — Ann Lam

(57) ABSTRACT

The invention relates to an ingestible, implantable or wearable medical device comprising a microarray which comprises a bioactive agent capable of interacting with a disease marker biological analyte; a reservoir which comprises at least one therapeutic agent and is capable of releasing the therapeutic agent(s) from the medical device; and a plurality of microchips comprising a microarray scanning device capable of obtaining physical parameter data of an interaction between the disease marker biological analyte with the bioactive agent; a biometric recognition device capable of comparing the physical parameter data with an analyte interaction profile; optionally a therapeutic agent releasing device capable of controlling release of the therapeutic agent from the reservoirs; an interface device capable of facilitating communications between the microarray scanning device, biometric recognition device and the therapeutic agent releasing device; and an energy source to power the medical device. Specifically, the invention relates to a medical device capable of detecting an analyte in a bodily fluid comprising at least one microneedle capable of obtaining a sample of a bodily fluid, a first microchannel through which the sample flows and is in fluid communication with the at least one microneedle, a second microchannel in fluid communication with the first microchannel, through which a buffer flows, wherein the second channel comprises a microarray with a bioactive agent, a microarray scanning device to detect an interaction between the bioactive agent and the analyte in the bodily fluid; and an interface device.

14 Claims, 13 Drawing Sheets

(51) Int. Cl.
   *A61B 5/1486* (2006.01)
   *A61M 5/142* (2006.01)
   *A61M 5/145* (2006.01)
   *A61M 5/172* (2006.01)
   *G01N 35/00* (2006.01)

(56) References Cited

U.S. PATENT DOCUMENTS

| | | | |
|---|---|---|---|
| 4,793,825 A | 12/1988 | Benjamin et al. | |
| 5,279,607 A | 1/1994 | Schentag et al. | |
| 5,624,850 A | 4/1997 | Kumar et al. | |
| 5,716,852 A | 2/1998 | Yager et al. | |
| 5,797,898 A | 8/1998 | Santini et al. | |
| 5,801,057 A | 9/1998 | Smart et al. | |
| 5,807,375 A | 9/1998 | Gross et al. | |
| 5,820,548 A | 10/1998 | Sieben et al. | |
| 5,832,296 A | 11/1998 | Wang et al. | |
| 5,848,991 A | 12/1998 | Gross et al. | |
| 5,874,214 A | 2/1999 | Nova et al. | |
| 5,961,923 A | 10/1999 | Nova et al. | |
| 5,976,896 A | 11/1999 | Kumar et al. | |
| 6,123,861 A | 9/2000 | Santini et al. | |
| 6,200,814 B1 | 3/2001 | Malmqvist et al. | |
| 6,221,677 B1 | 4/2001 | Wu et al. | |
| 6,245,057 B1 * | 6/2001 | Sieben et al. | 604/891.1 |
| 6,319,668 B1 | 11/2001 | Nova et al. | |
| 6,340,588 B1 | 1/2002 | Nova et al. | |
| 6,352,854 B1 | 3/2002 | Nova et al. | |
| 6,368,275 B1 | 4/2002 | Sliwa et al. | |
| 6,372,428 B1 | 4/2002 | Nova et al. | |
| 6,464,687 B1 | 10/2002 | Ishikawa et al. | |
| 6,482,593 B2 | 11/2002 | Walt | |
| 6,491,666 B1 | 12/2002 | Santini, Jr. et al. | |
| 6,503,231 B1 | 1/2003 | Prausnitz et al. | |
| 6,527,762 B1 | 3/2003 | Santini et al. | |
| 6,542,717 B1 | 4/2003 | Zimmerman et al. | |
| 6,544,732 B1 | 4/2003 | Chee et al. | |
| 6,551,838 B2 * | 4/2003 | Santini et al. | 436/174 |
| 6,560,471 B1 | 5/2003 | Heller et al. | |
| 6,632,216 B2 | 10/2003 | Houzego et al. | |
| 6,649,358 B1 | 11/2003 | Parce et al. | |
| 6,832,296 B2 | 12/2004 | Hooker | |
| 6,929,636 B1 | 8/2005 | Von Alten | |
| 6,966,880 B2 | 11/2005 | Boecker et al. | |
| 7,039,453 B2 | 5/2006 | Mullick et al. | |
| 7,112,444 B2 | 9/2006 | Beebe et al. | |
| 7,201,872 B2 | 4/2007 | Meron | |
| 7,291,497 B2 * | 11/2007 | Holmes et al. | 435/287.2 |
| 7,459,305 B2 * | 12/2008 | Levy | 435/287.2 |
| 7,807,197 B2 | 10/2010 | Lee et al. | |
| 8,055,329 B2 | 11/2011 | Kimchy et al. | |
| 8,101,402 B2 * | 1/2012 | Holmes | 435/287.2 |
| 8,202,697 B2 * | 6/2012 | Holmes | 435/7.1 |
| 2001/0051766 A1 | 12/2001 | Gazdzinski | |
| 2002/0001854 A1 | 1/2002 | Lee | |
| 2002/0034757 A1 | 3/2002 | Cubicciotti | |
| 2002/0055127 A1 | 5/2002 | Gindilis | |
| 2002/0072733 A1 | 6/2002 | Flaherty | |
| 2002/0132226 A1 * | 9/2002 | Nair et al. | 435/4 |
| 2003/0014362 A1 | 1/2003 | Yim | |
| 2003/0049833 A1 | 3/2003 | Chen et al. | |
| 2003/0049865 A1 | 3/2003 | Santini, Jr. et al. | |
| 2003/0061687 A1 | 4/2003 | Hansen et al. | |
| 2003/0069560 A1 | 4/2003 | Adamis et al. | |
| 2003/0097092 A1 | 5/2003 | Flaherty | |
| 2003/0104590 A1 | 6/2003 | Santini et al. | |
| 2003/0117491 A1 | 6/2003 | Avni et al. | |
| 2003/0143551 A1 | 7/2003 | Cattell | |
| 2003/0148362 A1 | 8/2003 | Luka | |
| 2003/0153900 A1 | 8/2003 | Aceti et al. | |
| 2003/0167000 A1 | 9/2003 | Mullick et al. | |
| 2003/0191430 A1 | 10/2003 | D'Andrea et al. | |
| 2003/0214057 A1 | 11/2003 | Huang | |
| 2004/0005582 A1 | 1/2004 | Shipwash | |
| 2004/0096959 A1 | 5/2004 | Stiene et al. | |
| 2004/0213825 A1 | 10/2004 | Levy | |
| 2005/0009101 A1 | 1/2005 | Blackburn | |
| 2005/0019836 A1 | 1/2005 | Vogel et al. | |
| 2005/0064529 A1 | 3/2005 | Kwon | |
| 2005/0100937 A1 | 5/2005 | Holmes | |
| 2005/0136548 A1 | 6/2005 | McDevitt et al. | |
| 2005/0147559 A1 | 7/2005 | Von Alten | |
| 2005/0209565 A1 | 9/2005 | Yuzhakov et al. | |
| 2005/0249633 A1 | 11/2005 | Blatt et al. | |
| 2005/0255001 A1 | 11/2005 | Padmanabhan et al. | |
| 2005/0255600 A1 | 11/2005 | Padmanabhan et al. | |
| 2006/0019319 A1 | 1/2006 | Billadeau et al. | |
| 2006/0029924 A1 | 2/2006 | Brewster et al. | |
| 2006/0062852 A1 | 3/2006 | Holmes | |
| 2006/0106316 A1 | 5/2006 | Palti | |
| 2006/0182738 A1 | 8/2006 | Holmes | |
| 2006/0211933 A1 | 9/2006 | Zimmermann et al. | |
| 2007/0166195 A1 | 7/2007 | Padmanabhan et al. | |

FOREIGN PATENT DOCUMENTS

| | | |
|---|---|---|
| WO | WO 94/01165 A1 | 1/1994 |
| WO | WO 01/35928 A1 | 5/2001 |
| WO | WO 01/64344 A2 | 9/2001 |
| WO | WO 01/64344 A3 | 3/2002 |
| WO | WO 03/066128 A2 | 8/2003 |
| WO | WO 03/066128 A3 | 12/2003 |
| WO | 2004107972 A | 12/2004 |

OTHER PUBLICATIONS

Office action dated Feb. 17, 2009 for U.S. Appl. No. 11/202,231.
Office action dated Feb. 22, 2008 for U.S. Appl. No. 11/202,231.
Office action dated Mar. 3, 2011 for U.S. Appl. No. 11/202,206.
Office action dated Mar. 7, 2006 for U.S. Appl. No. 10/937,872.
Office action dated Mar. 16, 2011 for U.S. Appl. No. 11/202,231.
Office action dated Mar. 18, 2008 for U.S. Appl. No. 11/202,206.
Office action dated Mar. 22, 2010 for U.S. Appl. No. 11/202,206.
Office action dated Apr. 18, 2007 for U.S. Appl. No. 10/937,872.
Office action dated Jun. 21, 2007 for U.S. Appl. No. 11/202,231.
Office action dated Jul. 28, 2009 for U.S. Appl. No. 11/202,206.
Office action dated Sep. 1, 2005 for U.S. Appl. No. 10/937,872.
Office action dated Oct. 26, 2006 for U.S. Appl. No. 10/937,872.
Office action dated Nov. 5, 2009 for U.S. Appl. No. 11/202,231.
Office action dated Nov. 22, 2011 for U.S. Appl. No. 11/202,231.
Office action dated Dec. 19, 2008 for U.S. Appl. No. 11/202,206.
Bawendi, et al. The quantum-mechanics of larger semiconductor clusters. Annu. Rev. Phys. Chem. 1990; 41:477-496.
Bhatia, et al. Use of thiol-terminal silanes and heterobifunctional crosslinkers for immobilization of antibodies on silica surfaces. Anal Biochem. 1989; 178(2):408-13.
Bruchez, et al. Semiconductor nanocrystals as fluorescent biological labels. Science. 1998; 281(5385):2013-6.
Celebre, et al. A comparative study of efficiencies of fibre optic and prism TIRF sensors. Meas. Sci. Technol. 1992; 3:1166-1173.
Chan, Quantum dot bioconjugates for ultrasensitive nonisotopic detection. Science. 1998; 281(5385):2016-8.
Chang, et al. Micromachining & Microfabrication. SPIE Optical Engineering Press. Bellingham, Wash. 1997. (Cover pages and table of contents only).
Charles, et al. Synthesis of a fluorescent analog of polychlorinated biphenyls for use in a continuous flow immunosensor assay. Bioconjug Chem. 1995; 6(6):691-4.
Duffy, et al. Rapid Prototyping of Microfluidic Systems in Poly(dimethylsiloxane). Analytical Chemistry. 1998; 70(23):4974-4984.
Harrison's Principles of Internal Medicine, Part 2 Cardinal Manifestations of Disease, Ch. 60 (12th ed. 1991; pp. 338-343.).
International search report dated Jul. 4, 2005 for PCT Application No. US2004/029462.
Jaeger. Introduction to Microelectronic fabrication. Addison-Wesley Publishing Co. Reading Mass. 1988. (Cover pages and table of Contents only).

(56) References Cited

OTHER PUBLICATIONS

Mukerjee, et al. Microneedle array for transdermal biological fluid extraction and in situ analysis. Sensors and Actuators A. 2004; 114:267-275.

Preininger, et al. Polymer-coated optical fibres for application in a direct evanescent wave immunoassay. Analytica Chimica Acta, 2000; 403, 67-76.

Rai-Choudhury, ed., Handbook of Microlithography, Micromachining & Microfabrication. SPIE Optical Engineering Press. Bellingham, Wash. 1997. (Cover pages and table of contents only).

Runyan, et al. Semiconductor integrated circuit processing technology. Addison-Wesley Publishing Co., Reading Mass. 1990. (Cover pages and table of contents only).

Sapsford, et al. Demonstration of four immunoassay formats using the array biosensor. Anal Chem. 2002; 74(5):1061-8.

Scheurle, et al. HER-2/neu expression in archival non-smaill cell lung carcinomas using FDA-approved hercep test. Anticancer Res. 2000; 20:2091-2096.

Tedeschi, et al. Antibody immobilisation on fibre optic TIRF sensors. Biosens Bioelectron. 2003; 19(2):85-93.

\* cited by examiner 100 micrometer diameter microneedle is roughly the diameter of human hair An array of silicon microneedles The first and second microchannels that are in fluid communication with one another. Only small molecules will diffuse across the diffusional interface to the microarray i.e. functionalized sensor surface. Fluorescent detection by a TIRF spectrometer does not extend beyond the diffusional interface.

Schematic diagram of fiber optic TIRF sensor. Incoming laser light is directed through the output leg of a 50:50 fiber optic splitter onto the functionalized fiber. Emitted fluorescence couples back into the fiber and propagates towards the detector with little interference from the laser light.

abs. λ$_{max}$ 665 nm. fluoresc. λ$_{max}$ 690 nm

Diffusional Separation Data

MEDICAL DEVICE FOR ANALYTE MONITORING AND DRUG DELIVERY

This application is a continuation application of U.S. Ser. No. 11/202,206, filed on Aug. 12, 2005, now U.S. Pat. No. 8,101,402 which is a divisional application of U.S. patent application Ser. No. 10/937,872, filed on Sep. 10, 2004, now U.S. Pat. No. 7,291,497, which claims the priority of U.S. provisional application 60/501,847, filed on Sep. 11, 2003.

BACKGROUND OF THE INVENTION

1. Field of the Invention

This invention relates to the fields of diagnosis and drug delivery. More particularly it relates to medical devices and methods capable of monitoring levels of a bodily fluid analyte and optionally releasing of appropriate therapeutic agents.

2. Background

"Point of care" devices that are capable of detecting biological macromolecular activity or drug concentration levels are in high demand because they eliminate the need for patient lab visits, thus providing savings in both time and expense. One of the most valuable aspects of modern microarray technology is the ability to detect biological macromolecular dysfunction, malformation or mutation resulting in disease. However, this capability has not been fully exploited because such arrays have not been incorporated into ingestible, implantable or wearable point of care devices. Modern microarray technology is limited to characterization of biological macromolecules and their metabolites by analysis of immobilized analytes stabilized on slides to be inserted into a machine or analyzed manually outside of living organisms.

Because whole blood contains cells, platelets, a myriad of proteins and other macromolecules, assays involving blood typically require pre-processing of the sample to remove these components. Integrating pre-processing steps into a point of care device drives up the cost of the device itself, thus making use of the device financially unviable. For example, some devices currently on the market using whole blood in their assays; among them are Boehringer Mannheim's Reflotron™ system for measuring blood borne analytes (most notably cholesterol) and the iStat™ (iStat Inc.), which performs a number of critical care assays, including electrolytes, general chemistries, blood gases and hematology. The Reflotron™ relies on dry chemistry technology in which enzymes or other reactive elements are immobilized on the surface of a test strip. The assay is a calorimetric activity assay in which the reaction produces a color change and is thus indicative of the amount of analyte present. The iStat™ relies on electrochemical detection to produce a signal. In either case, a blood sample is taken separately (typically by a finger prick) and then placed on the chip (or cartridge in the case of the iStat), where the reaction occurs and is analyzed by an external detection unit. These existing monitoring systems are insufficient and inconvenient as they usually require the user to prick themselves and multiple steps to obtain a result. As such, there is a need for a wearable device that can repeatedly, automatically and accurately monitor bodily fluids such as blood.

Point of care devices are also useful in certain situations where systemic biological samples such as blood, urine or stool, cannot provide adequate information as to subtle molecular changes at the situs of disease. In such a case, even if the clinician could pinpoint the exact situs of an ailment, obtaining a biological sample for analysis comes only at great risk, pain and expense for the patient. Additionally, a point of care device would be desirable where the systemic administration of drug agents, such as by transdermal or intravenous means, treats the body as a whole even though the disease to be treated may be localized. Here, systemic administration may not be desirable because the drug agents often have unwanted effects on parts of the body that are not intended to be treated, or because treatment of the diseased part of the body requires a high concentration of drug agent that may not be achievable by systemic administration. For example, when administered to a patient systemically, some drugs (e.g., chemotherapeutic drugs such as those used to treat cancer and other proliferative disorders) may cause undesirable side effects. It is therefore often desirable to detect disease and administer drug agents at a localized sites within the body.

As such there is a demand for point of care devices capable of detecting biological macromolecular activity or drug concentration levels that may also administer a specific therapeutic agent at a localized site within the body in response to changes in biological macromolecular activity or drug concentration levels. All articles, publications and patents cited herein are incorporated by reference in their entirety for all purposes. Additionally, provisional patent application Ser. No. 60/501,847 filed Sep. 11, 2003, is hereby incorporated by reference.

SUMMARY OF THE INVENTION

One aspect of the invention relates to a medical device comprising a microarray which comprises a bioactive agent capable of interacting with a disease marker biological analyte; a reservoir which comprises at least one therapeutic agent and is capable of releasing the therapeutic agent(s) from the medical device; and a plurality of microchips comprising a microarray scanning device capable of obtaining physical parameter data of an interaction between the disease marker biological analyte with the bioactive agent; a biometric recognition device capable of comparing the physical parameter data with an analyte interaction profile; a therapeutic agent releasing device capable of controlling release of the therapeutic agent from the reservoirs; an interface device capable of facilitating communications between the microarray scanning device, biometric recognition device and the therapeutic agent releasing device; and an energy source to power the medical device.

In one embodiment of this aspect of the invention the device is coated and the coating is a biostable polymer which may have channels. In another embodiment of this aspect of the invention, the polymer is porous.

In a different embodiment, bodily fluids are transported through microfluidic lanes which move molecules by means of pressure differences over the microarray. In one embodiment, an osmotic pump is used to propel the fluids through the top portion of the device. In another embodiment fluid transport is powered by natural electric currents in the body conducted through Personal Area Network technology.

In yet another embodiment of this aspect of the invention, the microarray comprises microbeads. In another embodiment, the bioactive agent is a nucleic acid. In yet another embodiment, the bioactive agent is a polypeptide. In yet another embodiment, the bioactive agent is an immunoglobulin.

In an additional embodiment of the medical devices of the invention, the bioactive agent is fluorescently labeled. In another embodiment, the bioactive agent is fluorescently labeled with a nanocrystal.

In yet another embodiment, the disease marker biological analyte is a nucleic acid. In a further embodiment, the disease marker biological analyte is a polypeptide. In another embodiment, the disease marker biological analyte is an immunoglobulin.

In yet a further embodiment, the plurality of microchips comprise silicon germanium.

In another embodiment, the microarray scanning device comprises fiber optic elements.

In an additional embodiment, the analyte interaction profile is stored in the biometric recognition device. In an alternative embodiment, the analyte interaction profile is stored externally from the medical device.

In another embodiment, the medical device has a plurality of reservoirs. In an additional embodiment, the interface device comprises a personal area network.

In an additional embodiment, the energy source is a battery. In an alternate embodiment, the energy source is provided by a personal area network.

Another aspect of the invention relates to a method of detecting and treating a disease in a patient comprising administering to the patient a coated medical device comprising a microarray comprising a bioactive agent capable of interacting with a disease marker biological analyte; at least one reservoir comprising at least one therapeutic agent and capable of releasing the at least one therapeutic agent from the medical device; a plurality of microchips comprising a microarray scanning device capable of obtaining physical parameter data of an interaction between the disease marker biological analyte with the bioactive agent; a biometric recognition device capable of comparing the physical parameter data with an analyte interaction profile; a therapeutic agent releasing device capable of controlling release of the therapeutic agent from the reservoir; and an interface device capable of facilitating communications between the microarray scanning device, the biometric recognition device and the therapeutic agent releasing device; an energy source to power the medical device; and biocompatible coating enabling the medical device to be swallowed, pass through the patient's intestinal tract and be naturally excreted.

In one embodiment of the method the coating is a biostable polymer which may have channels. In another embodiment, the polymer is porous.

In yet another embodiment of the method, the microarray comprises microbeads. In another embodiment, the bioactive agent is a nucleic acid. In yet another embodiment, the bioactive agent is a polypeptide. In yet another embodiment, the bioactive agent is an immunoglobulin.

In an additional embodiment of the method of the invention, the bioactive agent is fluorescently labeled. In another embodiment, the bioactive agent is a fluorescently labeled with a nanocrystal.

In yet another embodiment of the method, the disease marker biological analyte is a nucleic acid. In a further embodiment, the disease marker biological analyte is a polypeptide. In another embodiment, the disease marker biological analyte is an immunoglobulin.

In yet a further embodiment of the method, the plurality of microchips comprise silicon germanium.

In another embodiment of the method, the microarray scanning device comprises fiber optic elements.

In an additional embodiment of the method, the analyte interaction profile is stored in the biometric recognition device. In an alternative embodiment, the analyte interaction profile is stored externally from the medical device.

In another embodiment of the method utilizes a plurality of reservoirs. In an additional embodiment of the method, the interface device comprises a personal area network.

In an additional embodiment of the method, the energy source is a battery. In an alternate embodiment, the energy source is provided by a personal area network.

In an additional embodiment of the method, the communications are monitored by an external computer. In another embodiment, the external computer directs release of the therapeutic agent.

Another aspect of the invention relates to a medical device capable of detecting an analyte in a bodily fluid comprising at least one microneedle capable of obtaining a sample of a bodily fluid, a first microchannel through which the sample flows and is in fluid communication with the at least one microneedle, a second microchannel in fluid communication with the first microchannel, through which a buffer flows, wherein the second channel comprises a microarray with a bioactive agent, a microarray scanning device to detect an interaction between the bioactive agent and the analyte in the bodily fluid; and an interface device capable of facilitating communications between said microarray scanning device and a biometric recognition device.

In one embodiment, the bodily fluid is blood. In another embodiment, the at least one microneedle is a plurality of microneedles. In yet another embodiment the microneedle is between about 10 and about 200 microns in diameter. In a further embodiment, the microneedle is capable of drawing about 100 microliters of blood. In another embodiment, the first microchannel is about 100 micrometers in diameter. In an additional embodiment, the second microchannel is about 100 micrometers in diameter.

In still a further embodiment, the analyte in the bodily fluid flowing through the first microchannel diffuses into the second microchannel and interacts with the bioactive agent. In another embodiment, the analyte in the bodily fluid flowing through the first microchannel diffuses into the second microchannel and competitively displaces labeled analyte from binding the bioactive agent. In a further embodiment, the labeled analyte is provided in a predetermined amount. In another embodiment, the labeled analyte is labeled with a fluorescent moiety. In yet another embodiment, the microarray is a portion of the second microchannel having a coating of an antibody specifically binding the analyte in the bodily fluid. In a further embodiment, the microarray scanning device comprises a total internal reflection fluorescence (TIRF) spectrometer.

In another embodiment of this aspect of the invention the biometric recognition device is located outside of the device and the communication is through wireless transmission. In another embodiment, the analyte is insulin and the bioactive agent is an antibody specific for insulin. In yet a further embodiment, the analyte is glucose and the bioactive agent is an antibody specific for glucose. In still another embodiment, the device is a worn on the skin as a patch.

In a further embodiment of this aspect of the invention, the analyte is indicative of disease.

In another embodiment of this aspect of the invention, the medical device further comprises a reservoir having a therapeutic agent therein and a therapeutic agent releasing device, capable of controlling release of a therapeutic agent from a reservoir in response to an instruction from the biometric recognition device. In another embodiment, the analyte is glucose and the therapeutic agent is insulin. In a further embodiment, the analyte and the therapeutic agent are the same.

In another embodiment of this aspect of the invention, the medical device has at least one disposable assay device which comprises the at least one microneedle, the first microchannel and the second channel and has a non-disposable assay reader device comprising the microarray scanning device the interface device. In a further embodiment, the assay device and assay reader device are in optical communication with one another. In yet a further embodiment there are a plurality of disposable assay devices fitted in a single assay reader device.

In another embodiment, the microarray comprises an uncladded portion of a single glass optical fiber functionalized with the bioactive agent wherein the uncladded portion of single glass optical fiber is in fluid contact with the second microchannel. Alternatively, the microarray may comprise a plurality a uncladded portions of single glass optical fibers functionalized with the bioactive agent wherein the uncladded portions of single glass optical fibers are in fluid contact with the second microchannel.

Additional advantages of the present invention will become readily apparent to those skilled in this art from the following detailed description, wherein only the preferred embodiment of the invention is shown and described, simply by way of illustration of the best mode contemplated of carrying out the invention. As will be realized, the invention is capable of other and different embodiments, and its several details are capable of modifications in various obvious respects, all without departing from the invention. The present invention may be practiced without some or all of these specific details. In other instances, well known process operations have not been described in detail, in order not to unnecessarily obscure the present invention. Accordingly, the drawings and description are to be regarded as illustrative in nature, and not as restrictive.

DETAILED DESCRIPTION OF THE INVENTION

In its most basic form, the invention relates to a medical device which acts as a sensor to qualitatively and/or quantitatively detect analytes in bodily fluids. Such analytes may potentially be indicative of disease or be drugs or drug metabolites. Additionally, the device may be capable of releasing therapeutic agent(s) in response to sensory inputs. As such, it may further provide continuous diagnosis and medication. The inventive devices may be implantable, ingestible or worn on the skin as a patch.

The devices are capable of sampling analytes in biological fluids. Biological fluids include but are not limited to blood, serum, urine, gastric and digestive juices, tears, saliva, stool, semen, and interstitial fluids derived from tumorous tissues.

Bodily fluid drawn into the medical device is brought into contact with a microarray which samples biological analytes in bodily fluids. Fluid may be released from the medical device and can contain therapeutic agent(s) released in response to the presence or absence of a particular analyte. Most preferably, bodily fluid movement into or out of the medical device is facilitated by a pump, such as a microfluidic or osmotic pump. In another embodiment, molecular transport is conducted through pressurized microfluidic lanes which cause fluids to flow over a microarray. In yet another embodiment molecules are transported by natural electric currents conducted by Personal Area Network (PAN) transmitters or piezoelectric or magnetic sensors.

With respect to implantable embodiments, the device may be sealed to the tip of a catheter endoscope for realtime analysis and modeling of drug concentrations inside the body. For example the devices may associated with a vascular, gastric or biliary stent, for example. In another embodiment, the device is sealed to the inside of the stent. In another embodiment the devices are packaged in a polymer system which allows it to be implanted into the body, lenses which could be placed in the back of the eye, external sensors of gases and air pollution, and other objects in which real time monitoring is called for.

Figure 2:
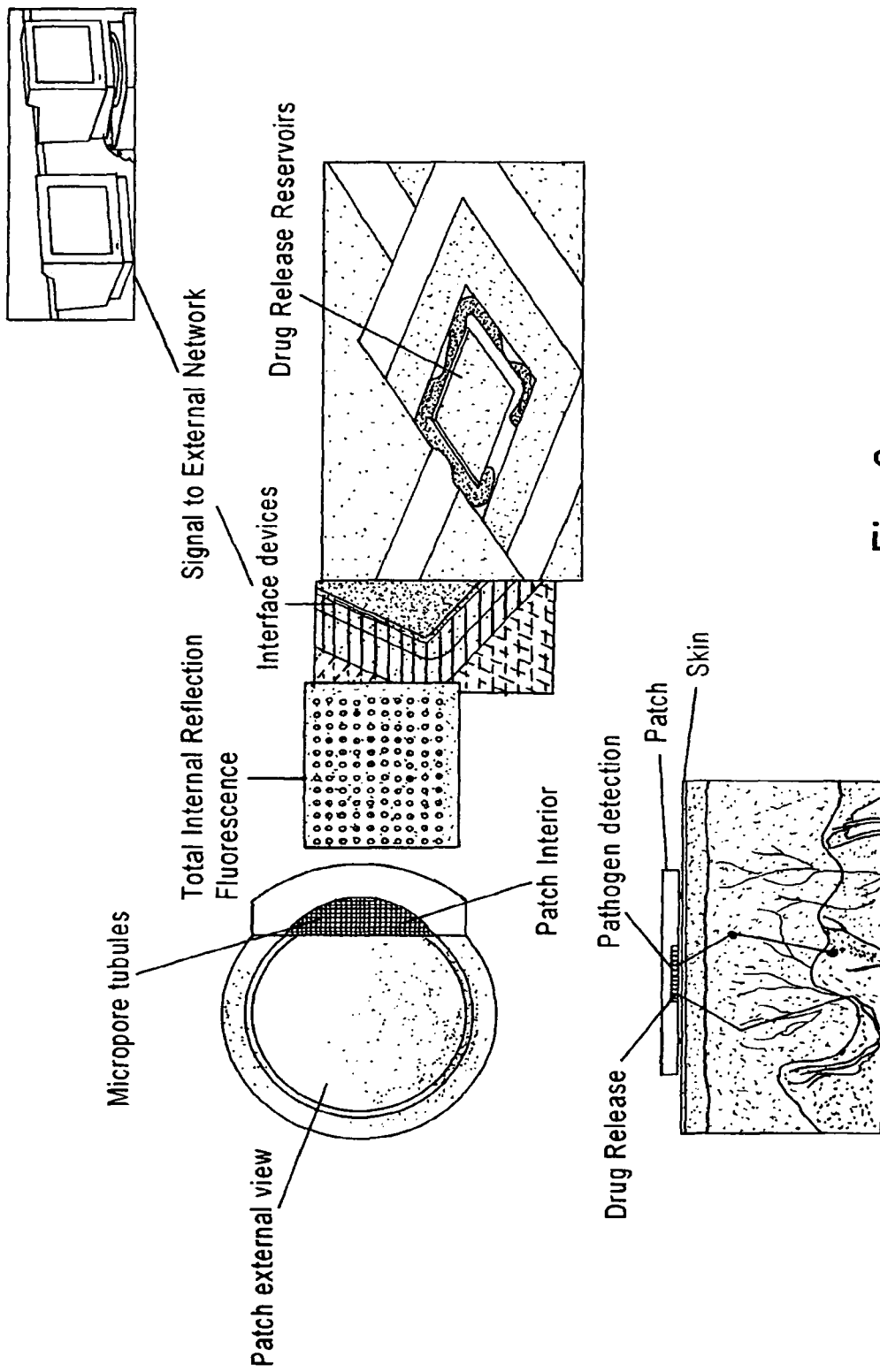
FIG. 2. illustrates the inventive device in its external patch embodiment. It is worn on the skin and may be capable of releasing a therapeutic agent. Additionally, it is capable of interfacing with an external network.
Figure 3:
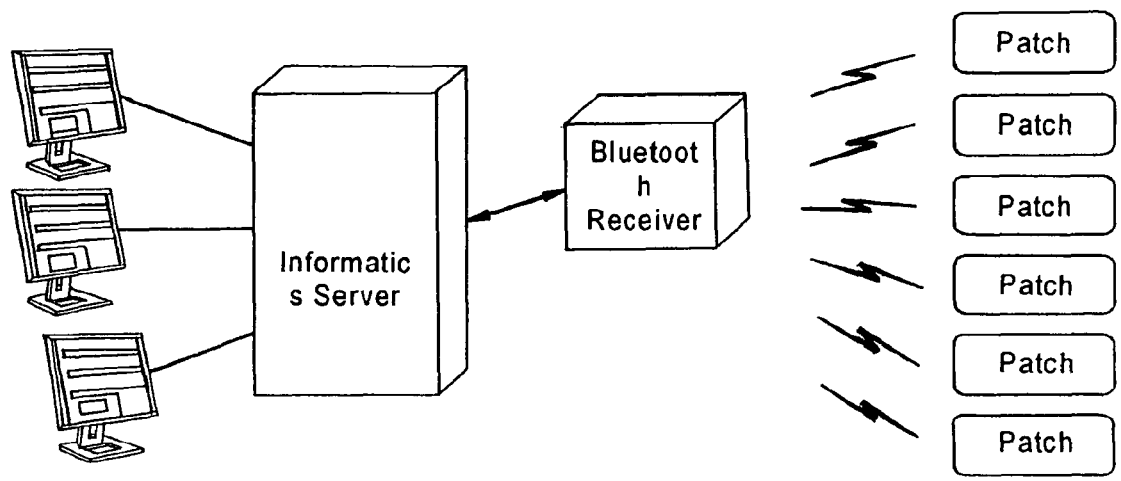
FIG. 3. illustrates a plurality of medical devices, here in the form of patches, in wireless communication with an external server. The external server may contain a biometric recognition device and pharmacokinetic database of physical parameters of the interaction between a bioactive agent and an analyte.

In one embodiment, the device is in the form of a patch. FIG. 2. Preferably, the device is an adhesive patch that is applied externally to the skin to be used as a monitor of whole blood analytes. More preferably, blood analytes are drugs whose levels are monitored by the patch. Such drugs have narrow therapeutic ranges and are present in micromolar concentrations in the blood. Most preferably, the concentration and/or identity of target analyte molecules in the blood is measured directly on the patch and such information can then be transmitted to internal or external data storage systems.

Figure 4A:
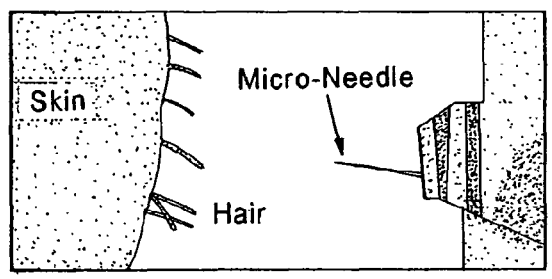
FIG. 4. (a) 100 micrometer diameter microneedle is roughly the diameter of human hair. (b) An array of silicon microneedles.
Figure 4B:
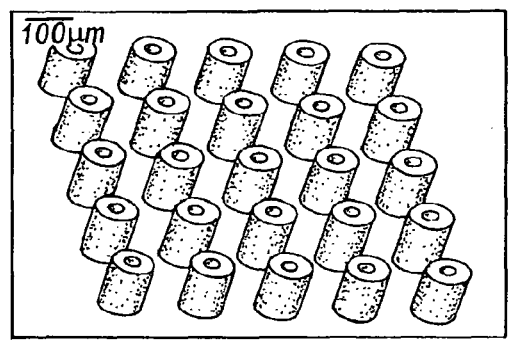

It is envisaged that the patch draws blood through the skin using at least one, if not a plurality, of microneedles. FIG. 4. Preferably, the microneedles are about the size of a human hair and have an integrated microreservoir or cuvette. The microneedle painlessly penetrates the skin and draws a tiny blood sample. More preferably, the microneedles collect about 0.01 to about 1 microliter, preferably, 0.05 to about 0.5 microliters and most preferably about 0.1-0.3 microliters of capillary blood and deliver them to a reservoir in the patch. Preferably, the microneedles are constructed out of silicon and are about 10 to about 200, preferably about 50 to 150 and most preferably 100 microns in diameter, making their application to the skin virtually painless. As the patch may most likely be placed on an area of the body less well perused than a fingertip, for example, capillary density is likely to be fairly low. In order to ensure that a capillary is actually struck by the needles, a plurality will be used for blood collection, as shown in FIG. 4. Preferably such microneedles are of the type marketed by Pelikan (Palo Alto, Calif.) and/or Kumetrix (Union City, Calif.) see also U.S. Pat. No. 6,503,231.

In one embodiment envisages using polymer needles, some of which are coated in porous gels and polymers which enable separation of targeted molecules based on size and or specificity. Gels include but are not limited to polychlorimeride and porous polycarbonate elastomers.

In general, microfabrication processes that may be used in making the microneedles disclosed herein include lithography; etching techniques, such as wet chemical, dry, and photoresist removal; thermal oxidation of silicon; electroplating and electroless plating; diffusion processes, such as boron, phosphorus, arsenic, and antimony diffusion; ion implantation; film deposition, such as evaporation (filament, electron beam, flash, and shadowing and step coverage), sputtering, chemical vapor deposition (CVD), epitaxy (vapor phase, liquid phase, and molecular beam), electroplating, screen printing, and lamination. See generally Jaeger, Introduction to Microelectronic Fabrication (Addison-Wesley Publishing Co., Reading Mass. 1988); Runyan, et al., Semiconductor Integrated Circuit Processing Technology (Addison-Wesley Publishing Co., Reading Mass. 1990); Proceedings of the IEEE Micro Electro Mechanical Systems Conference 1987-1998; Rai-Choudhury, ed., Handbook of Microlithography. Micromachining & Microfabrication (SPIE Optical Engineering Press, Bellingham, Wash. 1997). Alternatively, needles can be molded in silicon wafers and then plated using conventional wire cutting techniques with nickel, gold, titanium or various other biocompatible metals. In another embodiment, needles can be fashioned from biopolymers. Microneedles may be fabricated and employed for the claimed devices according to the methods of Mukerjee et al., Sensors and Actuators A: Physical, Volume 114, Issues 2-3, 1 Sep. 2004, Pages 267-275, which is hereby incorporated by reference in its entirety.

It is also preferable that although the device is capable of taking multiple measurements, a micro-needle is only to be used once. Preferably, multiple blood draws are carried out by a mechanical actuator that inserts and withdraws the needle and also disposes the used needle and reloads a new needle. The mechanical technologies developed and manufactured in very high volumes for very small disk drives (e.g. IBM micro drive) have a similar set of motion and low cost requirements. Preferably, a micro actuator is a MEMS (micro machined electromechanical system) device fabricated using semiconductor-like batch processes. Such actuators include nickel titanium alloy, neumatic, or piezo electric devices. The smallest needles are about 1-10, preferably about 2-6 and most preferably about 4 microns in thickness but over about 10-100, preferably about 30-60, and most preferably about 40 microns in height.

Alternatively, the needles are actuated by a spring-solenoid system in which a pin triggers the release of a miniaturized spring coiled tightly enough to generate sufficient force and range of motion necessary for actuation.

Figure 5A:
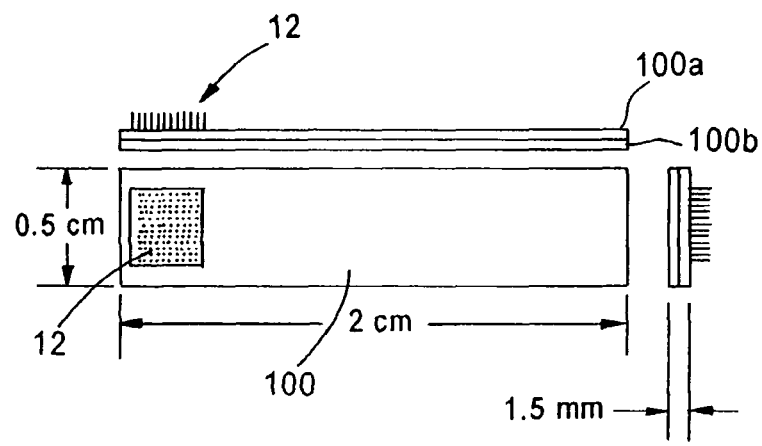
FIG. 5. (a) Illustrates various views of the inventive device in its patch embodiment 100. The exemplary patch is 2 cm in length and 0.5 cm in width. It is also has a thickness of about 1.5 mm. The patch contains a plurality of micro-needles 12 (b) Illustrates the internal features of the patch device. The device has a reservoir 13 into which a blood is pumped from the microneedles 12, a second reservoir containing a buffer 14 and common microchannel for laminar flow 15 which is the confluence of a buffer 15a and a blood inlet 15b, as well as a receptacle for waste 16. Additionally, the figure shows that the device may be separable in two components: A disposable layer having microneedles, microchannels and a microarray 100a and a non-disposable portion 100b in optical communication with the disposable portion having the microarray scanning device and other electronics.
Figure 5B:
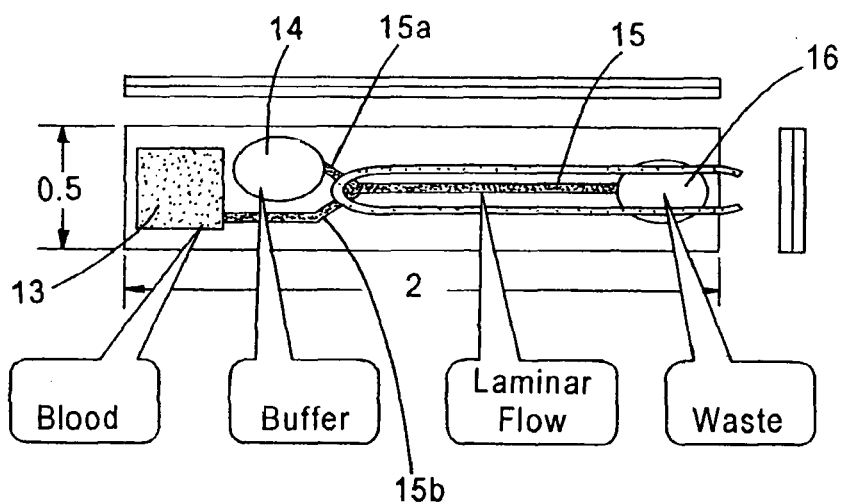
Figure 7:
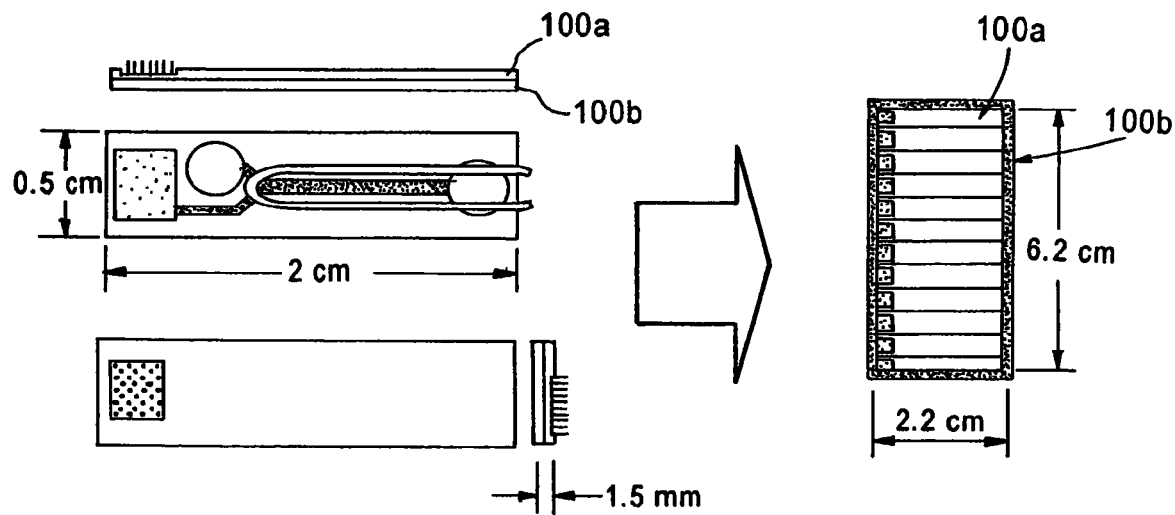
FIG. 7. Illustrates how a plurality of patches 100 may simultaneously be applied to a patient. Such a plurality of patches may then be sequentially activated to provide analyte detection of an extended period of time.

In one embodiment, the inventive patch device has two separable components: a disposable component having a plurality of microneedles, microchannels and a microarray (assay device); as well as a non-disposable component having a microarray scanning device and the ability to transmit results of an analyte interaction with a bioactive agent on a microarray to a biorecognition device, preferably by wireless communications, e.g., by Bluetooth® (assay reader device) (see FIG. 5). In this embodiment, a used disposable component may be removed from the non-disposable component while the non-disposable portion remains in place on the subject's body. A fresh disposable component having fresh needles may then be applied to the non-disposable portion already in place on a patient's body. The fresh disposable component may be capable to quantitatively or qualitatively detecting the same or a different analyte as the previously used disposable component. FIG. 7. In this embodiment it is preferable to apply fresh disposable components once the micro-needles of the used disposable component become clogged with blood clots, for example. The non-disposable component may also contain one or more disposable components. In this set up, each of the disposable components is capable simultaneously detecting a different analyte. Alternatively, the disposable components each detect the same analyte yet are sequentially actuated in such a manner as to sample bodily fluid, e.g. blood, in discrete periods of time. In this set up, the device detects analyte over an extended period of time by deploying one disposable component after the other over a period of time. Preferably, the device has 12 disposable components and can detect an analyte over a 24 hour period by deploying a new disposable component every 2 hours.

Figure 1:
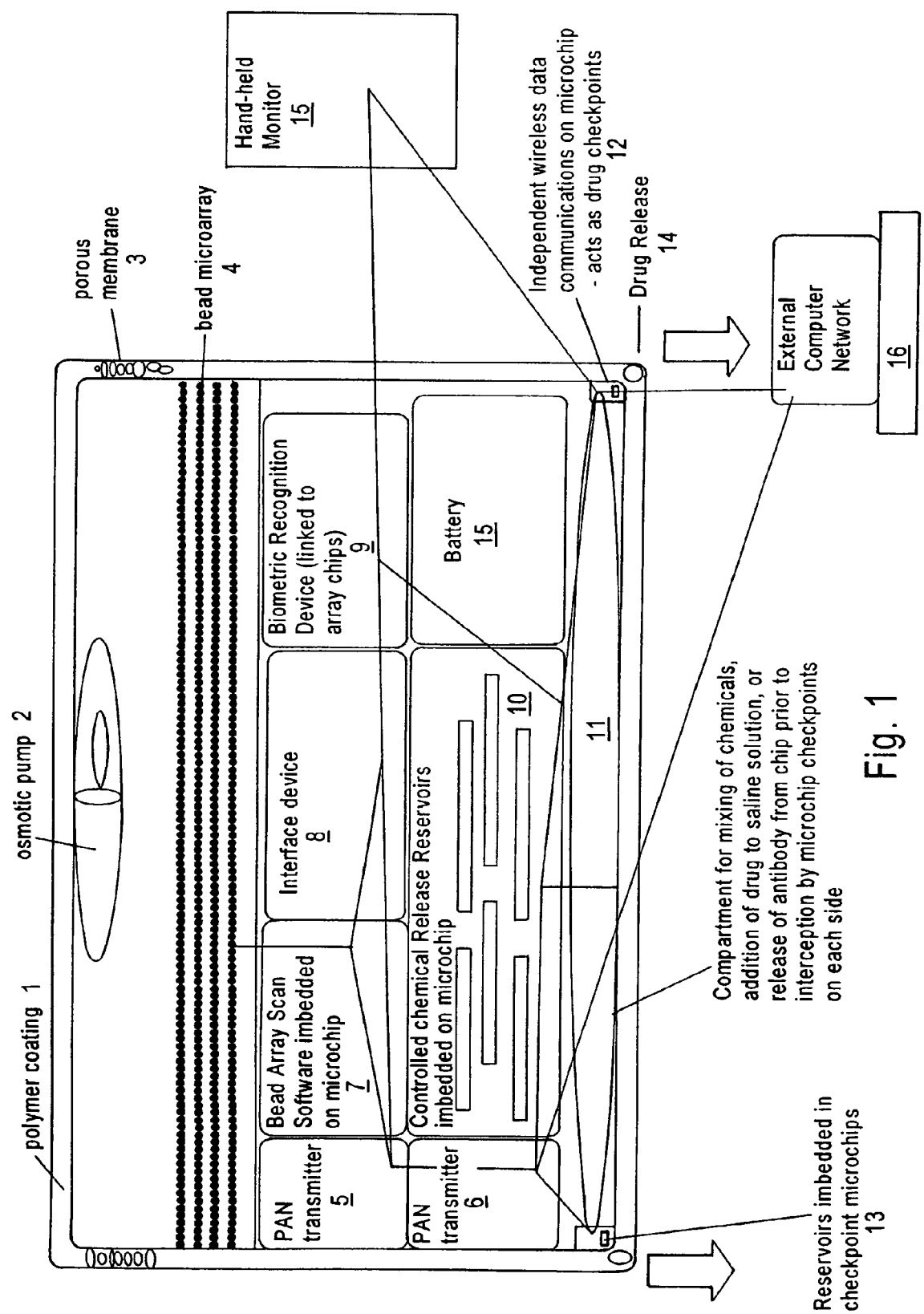
FIG. 1 is schematic drawing of an exemplary medical device of the invention. The device has a biostable polymer coating 1 as well as an osmotic pump in this preferred embodiment 2 to facilitate fluid movement through the device's porous coating 3. The device comprises a microarray 4 comprising a bioactive agent capable of interacting with a disease marker biological analyte; a reservoir 10 comprising a therapeutic agent and capable of releasing therapeutic agent from the medical device; and a plurality of microchips 5, 7, 8, 9, 6, 10, 12, 13 & 14 comprising; a microarray scanning device 7 capable of obtaining physical parameter data of an interaction between the disease marker biological analyte with the bioactive agent(s); a biometric recognition device 9 capable of comparing the physical parameter data with an analyte interaction profile; a therapeutic agent releasing device 10 capable of controlling release of therapeutic agent(s) from a plurality of reservoirs and checkpoints 13 & 14; and an interface device 8 capable of facilitating communications between the microarray scanning device 7, biometric recognition device 9 and the therapeutic agent releasing device 10; and an energy source to power the medical device 15. Additionally, the exemplary device contains transmitters for a personal area network 5 &6 and transmission pathways for communication between the PAN and a hand-held computer monitor 15 or external computer network 16. Additionally, the exemplary device contains a compartment 11 for the mixing of therapeutic agents prior to release.

In swallowable or implantable embodiments, it is preferable to coat the device with a "biostable polymer," which refers to those materials that do not undergo significant degradation upon prolonged exposure (e.g., up to one week, six months, a year, or longer) to bodily fluids, tissues, and the like and thus enables the device to pass through the entirety of the intestinal tract. It is preferred that fluid is drawn into and released from the medical device either through pores or channels in the polymer. FIG. 1.

The biostable coating materials of certain embodiments of this aspect of the invention are porous polymer materials that are characterized by interconnected pores of sufficient size to allow for the flow of bodily fluids into the medical device and the release therefrom, of therapeutic agents. The porous polymer materials are preferably characterized by an average pore diameter of at least about 5 microns, more preferably at least about 8 microns, and more preferably at least about 10 microns. Suitable polymers for use in embodiments wherein a porous structure is obtained by freeze-drying include any suitable biostable polymer, such as polyurethanes (including polyurethane dispersions), ethylene vinylacetate polymers, hydrogels such as crosslinked gelatin, dextran, polycarboxylic acids, cellulosic polymers, gelatin, polyvinylpyrrolidone, maleic anhydride polymers, acrylic latex dispersions, polyamides, polyvinyl alcohols, polyethylene oxides, glycosaminoglycans, polysaccharides, polyesters, polyacrylamides, polyethers, and blends and copolymers thereof.

The term "analyte" as used herein refers to antibodies, serum proteins, cholesterol, polysaccharides, nucleic acids, drugs and drug metabolites, etc., found in bodily fluids and tissues of the body. In another embodiment, the analyte is any biological analyte, marker, gene, protein, metabolite, or hormone or combination therein indicative of a biological state desirable for analysis to determine a physical state or condition. It is the purpose of the inventive device to qualitatively and/or quantitatively "detect" analytes in the bodily fluids. Preferably, such detection occurs periodically. Most preferably, it occurs in real time. In one embodiment, the analytes are present in micromolar to nanomolar concentrations and are highly potent chemotherapeutics, such as aminoglycocides or antibiotics, e.g., vancomycin, for which minute to minute monitoring is highly desirable because the analytes have narrow therapeutic ranges.

Through continuous monitoring of analyte levels in the body, the inventive devices allow the investigator to optimize therapeutic and dosage regimens and quickly develop pharmacokinetic models for experimental drugs. Target validation, lead optimization, and compound optimization (therapeutic range and toxicity studies) can now be done in a much faster and more accurate manner because monitoring trough concentrations enables rapid target elimination or validation of dosing schemes in addition to development of target leads. Thus, the inventive devices are useful in reducing the uncertainty as to whether to enter Phase II and III clinical trials thereby decreasing the time to registration and the overall costs of drug development. Moreover, the inventive devices provide a way of sensing drug concentrations of novel compounds in a fluorescent based assay, which remains the gold standard of sensitivity, and for the first time provides a targeted fluorescence based solution for monitoring of novel compounds.

The term "disease marker" as referred to herein is a detectable analyte, e.g., antibodies, serum proteins, cholesterol, polysaccharides, nucleic acids, drugs and drug metabolites, etc., found in bodily fluids and tissues which is present or absent in the body and known to be correlated with disease. Analytes, which allow for the detection of certain physiological conditions, can also be indicative of normal healthy physiology. These are referred to herein as "normal" or "healthy" biological analytes. Preferably, the biorecognition device of the invention detects a disease marker based on physical parameter data discerning between the physical characteristics of an interaction between 1) a disease marker biological analyte and a bioactive agent on the microarray and 2) a normal biological analyte with a bioactive agent on the microarray. Disease marker biological analytes allow for the detection of certain physiological conditions, e.g., infection, inflammation, autoimmune disease, cancer, etc. Disease markers presently known to those of skill and disease markers that will be known in the future are encompassed by this invention. The presence of a disease marker indicates the presence of disease and warrants the release of a therapeutic agent.

The disease marker biological analytes may be genes or their products which are over-expressed or over-active in cells undergoing unwanted proliferation. For example, the inventive device may be implanted into a tumor or a tissue suspected of containing a tumor such as a cavity or space left behind following a biopsy procedure. If the invention detects increased concentrations of such biological analytes or mutated over-active forms of such analytes, e.g., disease markers, a release of therapeutic agent(s) such as a cytotoxic agent is warranted. These disease marker biological analytes can be indicative of unwanted cellular proliferation such as cancer, neointimal proliferation resulting in arterial stenosis, psoriasis, etc. Disease marker biological analytes may be detected by analyzing gene expression in tissues and matching it to known tumor-gene expression patterns or comparing them to known normal expression patterns. In a preferred embodiment, the microarrays are used to detect the presence of a disease marker biological analyte as defined by the presence, absence or over-abundance of a particular nucleotide sequence, including a single nucleotide polymorphism (SNP), mRNA or a particular protein, such as an enzyme, an antibody or an antigen.

In one embodiment, the disease marker biological analytes are tumor specific antigens. For example, such antigens are expressed on the surface of or released from cancer cells, for example the tumor specific antigen MUC-1. Detection of MUC-1 expression through nucleic acid detection or by protein activity, can trigger the release of cytotoxic agents as therapeutic agents.

Another example relates to receptor tyrosine kinases (RTKs), which are important in the transduction of mitogenic signals. RTKs are large membrane spanning proteins which possess an extracellular ligand binding domain for growth factors such as epidermal growth factor (EGF), an intracellular portion which functions as a kinase to phosphorylate tyrosine amino acid residues on cytosol proteins thereby mediating cell proliferation. Various classes of receptor tyrosine kinases are known based on families of growth factors which bind to different receptor tyrosine kinases. Class I kinases such as the EGF-R family of receptor tyrosine kinases include the EGF, HER2-neu, erbB, Xmrk, DER and let23 receptors. These receptors are frequently present in common human cancers such as breast cancer, squamous cell cancer of the lung, bladder cancer, oesophageal cancer, gastrointestinal cancer such as colon, rectal or stomach cancer, leukaemia and ovarian, bronchial or pancreatic cancer. As further human tumor tissues are tested for the EGF family of receptor tyrosine kinases it is expected that its widespread prevalence will be established in other cancers such as thyroid and uterine cancer. Specifically, EGFR tyrosine kinase activity is rarely detected in normal cells whereas it is more frequently detectable in malignant cells. It has been more recently shown that EGFR is overexpressed in many human cancers such as brain, lung squamous cell, bladder, gastric, breast, head and neck, oesophageal, gynecological and thyroid tumours: Receptor tyrosine kinases are also important in other cell-proliferation diseases such as psoriasis. EGFR disorders are those characterized by EGFR expression by cells normally not expressing EGFR, or increased EGFR activation leading to unwanted cell proliferation, and/or the existence of inappropriate EGFR levels. The EGFR is known to be activated by its ligand EGF as well as transforming growth factor-alpha (TGF-α). The Her2-neu protein is also a member of the class I receptor tyrosine kinase (RTK) family. Her2-neu protein is structurally related to EGFR. These receptors share a common molecular architecture and contain two cysteine-rich regions within their cytoplasmic domains and structurally related enzymatic regions within their cytoplasmic domains. Accordingly, detection of abnormally high levels of RTK expression or signaling activity through nucleic acid detection or by protein activity can constitute a disease marker and can warrant the release of RTK inhibitors or cytotoxic agents as therapeutic agents.

The relatively high expression of genes that directly or indirectly inhibit chemotherapeutics constitute a disease marker for purposes of the invention. For example, high tumor expression of the DNA repair gene ERCC1 warrants release of genotoxic chemotherapeutic agents to a high local yet low systemic concentration. Thus, achieving concentrations that would not be safely sustained systemically. Additionally, high tumor levels of the gene DPD are known to inhibit 5-FU based chemotherapeutic regimen. Similarly, high tumor expression of the DPD warrants release of 5-FU chemotherapeutic agents to a high local yet low systemic concentration. Alternatively, the skilled artisan would also realize that high levels of ERCC1 or DPD may be indicative of chemotherapeutic resistance and that the use of genotoxic agents or 5-FU, respectively, may not be appropriate. In such a case, cytotoxic therapeutic agents other than genotoxic agents or 5-FU should be released from the device, respectively.

Alternatively, the device can be set up as to detect a panel of disease markers indicative of a disease such as cancer and release high local concentrations of cytotoxic agents such as a therapeutic agent.

In a further embodiment, disease marker biological analytes can be indicative of inflammation, which plays a crucial role in the etiology of inflammatory bowel disease, multiple sclerosis, childhood-onset diabetes, psoriasis, rheumatoid arthritis, etc. Such diseases previously required regular large systemic doses of potentially harmful steroids to address only localized inflammation. High localized concentrations of biological analytes such as TNF-alpha, IL-1, IL-8, IL-2, IL-3, MIF (IL-4), GM-CSF, INF-gamma, and TNF-beta are indicative of inflammation. The detection of abnormally high concentration of such biological analytes constitutes a disease marker and warrants localized release of anti-inflammatory drugs or antibodies as therapeutic agents.

In another embodiment, disease marker biological analytes can be indicative of infection by a microorganism. As such, disease markers can include viral or bacterial proteins or nucleic acids or fragments thereof. For example, detection of biological analytes such as bacterial toxins including exotoxins and enterotoxins as well as TSST-1, or other bacterial superantigen, or botulinum toxin, diphtheria toxin, anthrax protective antigen, anthrax edema factor, and anthrax lethal factor, etc., as well as viral proteins such as influenza hemagglutinin or neuraminidase, would constitute a disease marker indicative of infection and warrant localized release of antimicrobial drugs or toxin-specific antibodies as therapeutic agents.

Figure 8A:
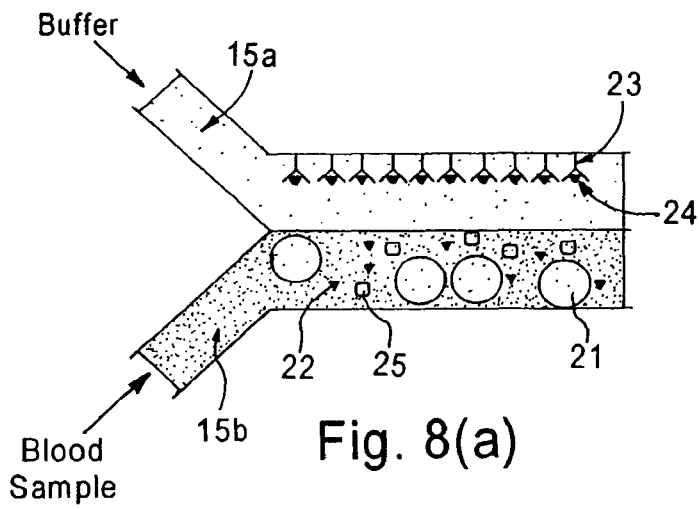
FIG. 8. (a) Side view of an exemplary laminar flow microchannel 15 in which blood is fed into one inlet 15b of a two inlet microchannel. The blood contains cells 21, a variety of proteins 25, and the analytes to be measured 22. The fluids flow in parallel streams with molecules passing across the interface only by diffusion. As shown in (b), only the small molecule analytes 22 reach the opposite wall where an equilibrium exchange takes place with fluorescently labeled analyte molecules 24 pre-bound to bioactive agents 23 on the surface. In this example, the channel wall coated with bioactive agents 23 constitutes the microarray.
Figure 8B:
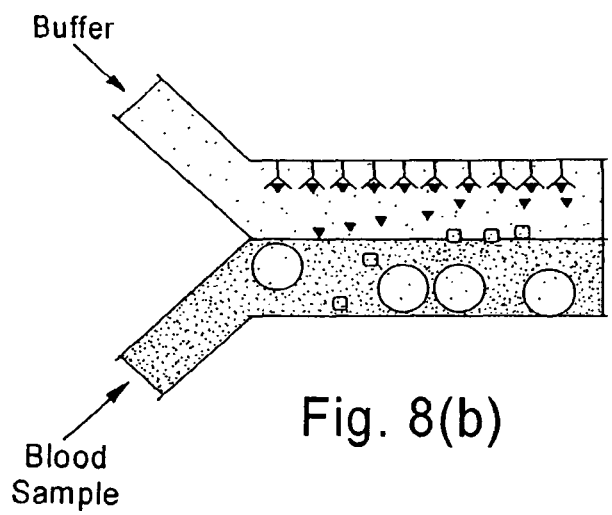
Figure 10:
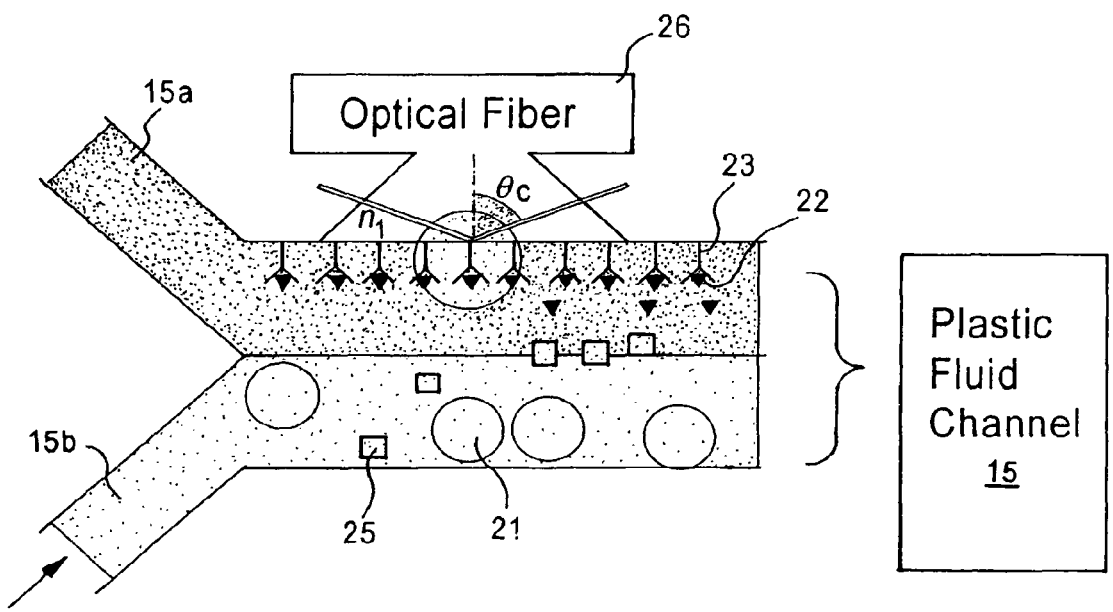
FIG. 10. Illustrates how an optical fiber 26 utilizes total internal reflection fluorescence to detect changes in fluorescence indicative of an interaction between a bioactive agent and an analyte that occur at the microarray. The optical fiber may have multiple configurations. For example, it may run parallel along the length of the laminar flow channel 15. Alternatively, a plurality fibers may terminate in the channel and themselves be coated with bioactive agent. The first 15a and second 15b microchannels are in fluid communication with one another. Only small molecules will diffuse across the diffusional interface to the microarray i.e. functionalized sensor surface. Fluorescent detection by a TIRF spectrometer does not extend beyond one wavelength beyond the surface.
Figure 11:
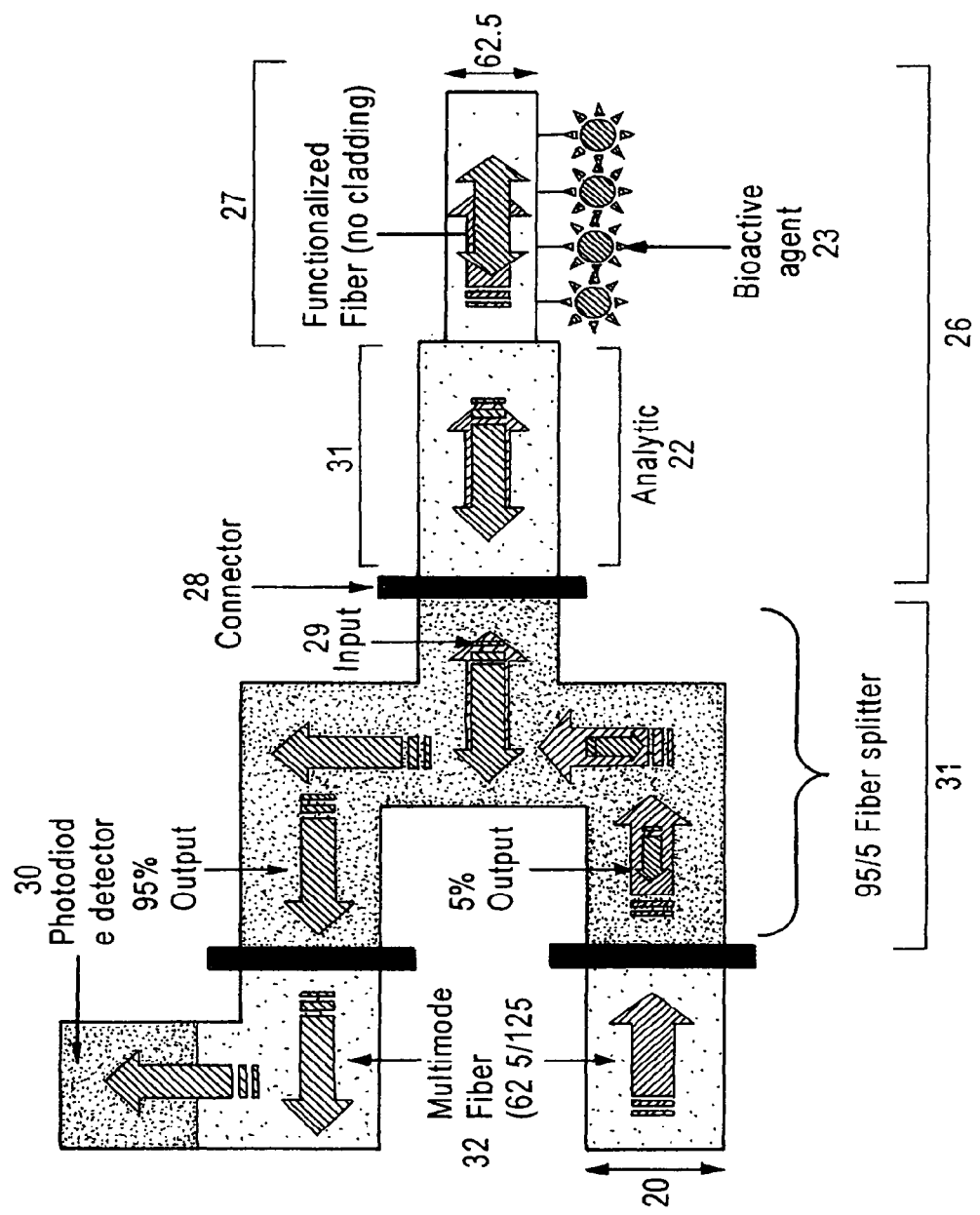
FIG. 11. Illustrates an optical fiber 26 that is part of an microarray. The optical fiber has a cladded 31 and an uncladded portion 27. The distal uncladded portion 27 is functionalized with a bioactive agent that interacts with a target analyte in the bodily fluid being assayed. The proximal end of the fiber 26 is in optical communication with a portion of the microarray scanning device. This contact is facilitated by a connector 28. Beyond the connector an input directs light to fiber splitter 31 which directs light returning to through the fiber to a detector such as a photodiode detector 30. As discussed elsewhere, the functionalized uncladded portion of the fiber 27 may constitute a portion of the wall of the laminar flow micro-channel 15 or a plurality of fibers may protrude into the channel 15.

Another aspect of the invention relates to a microarray. The microarray is the portion of the inventive devices that facilitates an interaction between an analyte and a bioactive agent. It its most basic embodiment, a "microarray" as defined herein may constitute any surface e.g. the wall of a microfluidic channel, covered or functionalized by a bioactive agent such that a microarray scanning device can detect interactions between a bioactive agent and an analyte. FIGS. 8, 10, 11. In another embodiment, the microarray is a collection of miniaturized test sites arranged on a surface that permits many tests, or assays, to be performed in parallel. In this context, the microarray is directly exposed to bodily fluids and/or tissues and may be able to simultaneously process a plurality of different assays and provide for the interaction of one or more bioactive agents with one or more biological analytes.

For example, the ability of a fluorescence-based array biosensor to measure and quantify the binding of an antigen to an immobilized antibody has been demonstrated using the four different immunoassay formats: direct, competitive, displacement, and sandwich. Sapsford et al., Anal Chem. 2002 Mar. 1; 74(5):1061-8 (incorporated by reference it its entirety), used a patterned array of antibodies specific for 2,4,6-trinitrotoluene (TNT) immobilized onto the surface of a planar waveguide and measured signals from different antigen concentrations simultaneously. For direct, competitive, and displacement assays, which are one-step assays, measurements were obtained in real time. Dose-response curves were calculated for all four assay formats, demonstrating the array biosensor's ability to quantify the amount of antigen present in solution.

In one embodiment of this aspect of the invention, the microarray is an area on a glass optical fiber that is functionalized with a bioactive agent. FIG. 11. In another embodiment, the microarray can have a plurality of glass optical fibers each functionalized with the same or different bioactive agents. In one particular embodiment, the bioactive agent of the microarray is a protein such as an antibody specific for an analyte. Two exemplary procedures may be employed for attaching protein bioactive agents to the glass optical fibers. The first is based on that developed by Bhatia et al. 1998, Analytical Biochemistry, 178 408-13. This involves functionalizing a surface with 3-mercaptopropyltrimethoxysilane. Following that, a cross-linker of N-γ-malemidobutylryloxysuccimide ester is used to attach the protein bioactive agent to the functionalized surface. The second procedure involves using a Dextran-based method described by Tedeschi et al. 2003, Biosensors and Bioelectronics, 19 85-93. This method uses glycidyl 3-(trimethoxysilyl)propyl ether to link the free hydroxyl groups on clean glass to the Dextran polymer. Protein bioactive agents are bound to the Dextran matrix following acidification of the carboxylic acid groups therein.

Optionally, the fiber may be coated with a steric membrane which separates targeted analytes.

Preferably, the fiber is directly inserted into the microneedle and the walls of the microneedles are coated with polymer gels for selectivity and specificity based binding events.

Figure 9:
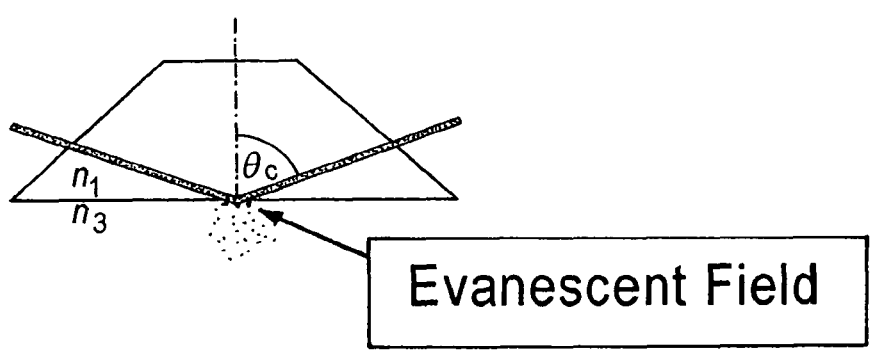
FIG. 9. Shows the concept of an evanescent field arising during total internal reflection. The evanescent field extends no more than one wavelength beyond the medium in which the light beam is traveling.

In embodiments utilizing glass optical fibers, a light source is utilized to excite fluorescently labeled bioactive agents and/or analytes such that fluorescence is detectably altered upon interaction with target analytes in bodily fluids. FIG. 11. A light source for excitation may be a laser module. Light may be launched into the optical fiber that contains a functionalized region, i.e. a region stripped of fiber cladding and chemically prepared for bioactive agent coating. FIGS. 9, 11. Due to the lack of cladding, an evanescent wave emanates from the fiber at point and incites fluorescence from fluorescent tagged bioactive agents or fluorescent tagged analytes bound to bioactive agents meant to be competitively displaced analytes in the bodily fluid being sampled. FIGS. 8, 11. Emitted light reenters the through the same fiber. Light returning into the fiber is detected by the microarray scanning device which may have a fiber optic splitter, bandpass filters capable of removing ambient background light, and a photodiode detector. A schematic of the described setup can be seen in FIG. 11.

Preferably, the bioactive agent is an antibody that is capable of specifically binding an analyte drug. Alternatively, the bioactive agent is an antigen that is capable of specifically binding serum antibodies. In this latter embodiment, the inventive devices can detect the production of specific types of antibodies produced in response to certain immunological stimuli, for example HIV or tuberculosis infection.

In another embodiment, the microarray facilitates interaction between 1) a disease marker biological analyte and a bioactive agent on the microarray and 2) a normal biological analyte with a bioactive agent on the microarray. In this context the bioactive agent differentially interacts with normal biological analyte and a disease marker biological analyte.

In another embodiment of the microarray, microbead arrays are used. By "microspheres" or "beads" or "particles" or grammatical equivalents herein is meant small discrete particles. The composition of the beads will vary, depending on the class of bioactive agent and the method of synthesis. Suitable bead compositions include those used in peptide, nucleic acid and organic moiety synthesis, including, but not limited to, plastics, ceramics, glass, polystyrene, methylstyrene, acrylic polymers, paramagnetic materials, thoria sol, carbon graphited, titanium dioxide, latex or cross-linked dextrans such as Sepharose, cellulose, nylon, cross-linked micelles and teflon may all be used. "Microsphere Detection Guide" from Bangs Laboratories, Fishers Ind. is a helpful guide, and is incorporated by reference in its entirety. The beads need not be spherical; irregular particles may be used. In addition, the beads may be porous, thus increasing the surface area of the bead available for either bioactive agent attachment or tag attachment. The bead sizes range from nanometers, e.g. 100 nm, to millimeters, e.g., 1 mm, with beads from about 0.2 micron to about 200 microns being preferred, and from about 0.5 to about 5 microns being particularly preferred, although in some embodiments smaller or larger beads may be used. Preferably, each microsphere comprises a bioactive agent.

Another aspect of the invention relates to a "bioactive agent". As used herein, it describes any molecule, e.g., protein, oligopeptide, small organic molecule, polysaccharide, polynucleotide, etc. which is used in the microarray and can interact with an analyte or differentially interact with normal and disease marker biological analytes present in bodily fluids or tissues. Bioactive agents may be labeled in such a way as to allow the microarray scanning device to ascertain certain physical parameters specific to the bioactive agent that are altered upon interaction with biological analytes.

In one embodiment, bioactive agents are fluorescently labeled and their fluorescence is detectably altered upon interaction with target analytes in bodily fluids. Alternatively, bioactive agents are pre-associated with labeled analytes such that the labeled analytes are competitively displaced by analytes in bodily fluids. In either case, the fluorescent characteristics of the microarray are altered upon microarray interaction with analytes in bodily fluids in such a manner that can be detected by a microarray scanning device.

Most preferably, either analytes or the bioactive agents are labeled with fluorescent nanocrystals. In comparison to organic dyes such as rhodamine, nanocrystals are approximately at least 20 times as bright, approximately at least 100 times as stable against photobleaching, and are approximately one-third as wide in the emission spectral linewidth. See, for example, Bruchez, et al., Science, 281:2013-2016 (1998); Chan and Nie, Science, 281:2016-2018 (1998); Bawendi et al., Annu. Rev. Phys. Chem. 41:477-496 (1990), and references cited therein, all of which are expressly incorporated by reference. The brightness, stability and narrowness of emission bandwidth all contribute to the ability to use a relatively large number of different colors as further described below (i.e. different size nanocrystals) while preserving the ability to resolve them from each other, and to resolve different quantities of each nanocrystal. In addition, the broad excitation spectrum allows many different nanocrystals to be excited by a common light source.

Bioactive agents may comprise functional groups necessary for structural interaction with proteins, particularly hydrogen bonding, and typically include at least an amine, carbonyl, hydroxyl or carboxyl group, and preferably at least two of the functional chemical groups. The bioactive agents often comprise cyclical carbon or heterocyclic structures and/or aromatic or polyaromatic structures substituted with one or more of the above functional groups. Bioactive agents are also found among biomolecules including peptides, nucleic acids, saccharides, fatty acids, steroids, purines, pyrimidines, derivatives, structural analogs or combinations thereof. Particularly preferred are nucleic acids and proteins.

"Interact with," as used herein refers to the ionic, covalent or hydrogen bonding, protein binding, nucleic acid hybridization, magnetic or hydrophobic attraction or other detectable and/or quantifiable association of an analyte and a bioactive agent on the microarray. "Differentially interact with," refers to the fact that a disease marker biological analyte will interact with a bioactive agent differently than a biological analyte indicative of normal physiology.

For example, the physical differences in interaction between 1) a disease marker biological analyte and a bioactive agent and 2) a normal biological analyte with a bioactive agent, are detectable by comparing the physical characteristics of the bioactive agent before, during or after interaction with the biological analyte. The detectable and/or quantifiable changes in bioactive agents upon interaction with a biological analyte are measurable through a series of physical parameters that depend on the nature of the bioactive agent employed. For example a detectable and/or quantifiable association may be evidenced by a shift in fluorescence intensity or wavelength due to binding or hybridization of the bioactive agent with a biological analyte.

In another embodiment, the binding (interaction), of a fluorescence-associated antibody on a microarray (bioactive agent), specific for a particular tumor-specific protein (disease marker biological analyte), results in a detectable shift in the intensity of the fluorescence of the bioactive agent. This stereotyped shift is indicative of the presence of a particular disease marker has previously been empirically determined while selecting the appropriate bioactive agent and target disease marker. Whereas non-specific binding may alter the fluorescence of the bioactive agent, it will not do so in a predicable and stereotyped way consistent with empirically determined results, and as such, will not be indicative of the presence of a disease marker biological analyte.

One feature of the invention relates to a "microarray scanning device". The physical parameter data of an interaction between analytes and the bioactive agents of the microarray are preferably "read" by a microarray scanning device and transmitted to a biorecognition device to determine the presence, absence, or quantity of analytes in bodily fluids. Preferably, a change in the physical characteristics of the microarray is detected upon interaction between the analyte and the bioactive agent. Alternatively, the scanning device is able to discern between the physical characteristics of an interaction between 1) a disease marker biological analyte and a bioactive agent on the microarray and 2) a normal biological analyte with a bioactive agent on the microarray.

"Physical parameter data" as referred to herein include information relating to interaction between analytes with bioactive agents on the microarray gathered by the microarray scanning device. Physical parameter data are transmitted to the biometric recognition device for analysis. The scanning device measures the physical, e.g., bio-electric, bio-magnetic, or biochemical, characteristics of interactions between biological analytes and the bioactive agent of the microarray by collecting data on one or more physical parameters relating to the interaction. Such parameters can include but are not limited to: fluorescence, binding strength, binding specificity, charge, etc.

Preferably, physical parameter data is stored in or compared to store profiles of physical parameter data in a bioinformatics system incorporating pharmacogenomic and pharmacokinetic data into its models for the determination of toxicity and dosing. Not only does this enable generation of data for clinical trials years prior to current processes but also enables the elimination of current disparities between apparent efficacy and actual toxicity of drugs through realtime continuous monitoring. For use in clinical trials during the go/no go decision process large scale comparative population studies can be conducted with the data stored on the data base through the information stored on the sever. This allows more patients to enter clinical trials in a safe fashion earlier. In another embodiment biomarkers discovered in human tissue studies can be targeted by the device for improved accuracy in determining drug pathways and efficacy in cancer studies.

In one embodiment of this feature, the microarrays are designed such that fiber optical elements are capable of emitting and receiving light at a particular wavelength to enable physical parameter data acquisition relating to interaction between the bioactive agent and analyte. In one example, the bioactive agents in the microarray are substantially saturated with a predetermined amount of fluorescently labeled analyte such that when they interact with unlabeled target analyte from a bodily fluid, the unlabeled analyte competitively displaces labeled analyte on the microarray to an extent commensurate with its concentration within the bodily fluid. As such, the microarray scanning device will detect and transmit a corresponding decrease in fluorescence on the microarray.

In another example, once the light has been absorbed by a dye on the bioactive agent, some light of varying wavelength and intensity returns, and is conveyed through either the same fiber or collection fiber(s) to the microarray scanning device for quantification. The interactions between the light conveyed by the optical fiber and the properties of a light absorbing dye provide an optical basis for both qualitative and quantitative determinations of changes in physical characteristics evidenced by the interaction between analytes and bioactive agents. See U.S. Pat. Nos. 6,482,593 and 6,544,732, which are incorporated by reference in their entirety. The biometric recognition device receives optical and fluorescence reception signal data, i.e. physical parameter data, and may instruct the therapeutic agent release device which dispenses specified therapeutic agents. An example of a suitable microarray scanning device is available commercially from several sources such as Illumina, Inc. San Diego, Calif.

One possibility for detecting differences in fluorescence resulting from interactions between analytes and bioactive agents, is by detecting emissions with a detector in the vicinity of the emitting molecules. Another possibility is coupling emissions into a fiber to be detected at the distal end by a detector. The fiber detecting the fluorescence may be the same fiber that delivers incoming light or a separate fiber exclusively for fluorescence detection. In the case of the latter, the detection fiber of the microarray must be stripped of cladding and treated for optimal coupling. Coupling back into a fiber may be more efficient using lenses adjacent to the fiber to focus emitted light more accurately. Detectors, as previously described, can include CCDs, PMTs, and most preferably photodiodes. The detectors will most likely be selective to the wavelength of emission by use of a bandpass filter. This detector may be located at the distal end of the delivery fiber An exemplary microarray optical glass fiber connected to a portion of a microarray scanning device is shown in FIG. 11. The figure depicts a functionalized uncladded fiber that extends into the micro-channels of the device and constitutes a portion of the microarray. The microarray of the inventive devices may include at least one or a plurality of optical fibers which can be in a bifurcated fiber optic system.

In the figure, the optic fiber is functionalized with an antibody bioactive agent and is set up to function as displacement assay similar to that of a fluorescence polarization immunoassay. Since fibers propagate light using the principles of total internal reflection (TIR), evanescent waves are emitted perpendicular to the fiber at bare regions (i.e. the functionalized region). An evanescent wave will be absorbed by any molecules present on the surface of the fiber, and a Stokes-shifted spectra is emitted by fluorophores (if present). The fiber is in optic communication with a fiber splitter which allows for light to pass into the functionalized uncladded fiber and re-routes light returning from the functionalized uncladded fiber to a photodiode detector.

In the patch embodiment of the inventive device having a disposable and a non-disposable component, the disposable component has micro-needles, micro-channels and a microarray. When inserted, the optic fibers of the microarray of the disposable component are in optical communication with a corresponding fiber splitter and photodiode detector, constituting a portion of the microarray scanning device of non-disposable component of the patch.

In another embodiment of the microarray scanning device, a change in the fluorescence of the microarray is detected upon its interaction with an analyte using a total internal reflection fluorescence (TIRF) spectrometer. The principle of TIRF is depicted schematically in FIG. 9, 10. Total internal reflection is an optical phenomenon which occurs when light propagating in a dense medium (such as glass) meets an interface with a less dense medium, such as the buffer depicted in FIG. 9. If the light meets the interface at a small angle, some of the light passes through the interface (is refracted) and some is reflected back into the dense medium. At a certain angle, all of the light is reflected. This angle is known as the critical angle, and its value depends on the refractive indices of the media. However, some of the energy of the beam propagates a short distance (preferably a few hundred nanometers) into the buffer, generating an evanescent wave. If this energy is not absorbed, it passes back into the glass where it can be detected. However, if a fluorophore molecule associated with a bioactive agent or labeled analyte, is within the evanescent wave it can absorb photons and be excited. In this way, it is possible to get fluorescence with a very low background of excitation light.

The levels of fluorescence from a single fluorophore are extremely low (hundreds to thousands of photons per second). However, it is preferably detected in two ways. The first is to use an intensified CCD camera which can produce an image, in which bound fluorophores will appear as bright spots. Alternatively, it is possible to image the fluorophore through a pinhole onto a photomultiplier tube (PMT), with which one can count the number of photons detected. Preferably, such a microarray scanning device utilizes an integrated optics system is employed such as the Texas Instruments Spreeta™ sensor. More preferably, the microarray scanning device makes use of surface plasmon resonance, a similar evanescent wave based technique to TIRF. In such a sensor, a polarized LED light source is used along with a photodetector array for measuring the position of reflected light.

Another feature of this aspect of the invention relates to a biometric recognition device which through analysis of the physical parameter data e.g. for example fluorophore image or photon counts, collected by the microarray scanning device determines the absence, presence or quantity of an analyte. When an analyte interacts with a bioactive agent on the microarray, the microarray scanning device conveys data on the physical parameters of the interaction to the biorecognition device which in turn, matches that data with a known analyte interaction profile to determine the presence, absence and/or quantity of an analyte.

In one embodiment, disease marker biological analytes interact with a bioactive agent on a microarray in stereotyped and predicable fashion and the interaction is evidenced by reproducible and predictable physical parameter data. Known data are referred to herein as an "analyte interaction profile." Such profiles will have been empirically established in vitro and the biometric recognition device may have access to both analyte interaction profiles of disease markers and normal analytes. The biometric recognition device receives raw physical parameter data from the microarray scanning device and compares that information with stored analyte interaction profiles. The biometric recognition device may have access to both analyte interaction profiles of disease markers and normal analytes.

The biometric recognition device is either located in the inventive medical device or it is located externally. Communication between the microarray scanning device and the biometric recognition device may be facilitated by a local area network (LAN) or a wireless local area network (WLAN), e.g. by Bluetooth® technology. Additionally, the biometric recognition device can also store analyte interaction profiles and build a pharmacokinetic database of accessible information in the form of analyte interaction profiles.

In a particularly preferred configuration for detecting and quantifying the presence of analytes, the device is a patch with microfluidic channels as shown in FIG. 5. The device has at least two inlets feeding into a main channel. Sample blood (containing the analyte) is fed into one inlet and the opposing inlet is fed by a buffer solution. At small dimensions, fluids flow in the absence of inertia and turbulent mixing; thus, the blood and buffer flow in parallel streams. The microchannels are preferably between about 50 and about 200 µm, more preferably about 75 and about 150 µm and most preferably about 100 µm in diameter.

Preferably, pumping the fluids through the channels in a controlled manner is done by wicking or a vacuum in which a membrane is broken by activation of the microneedles to create a pressurized pulling force which brings the fluid through. Channels may be produced by precision injection molding or laser etching.

Channel size as well as microarray surface chemistry may be adjusted to account for the size of the analytes measures. The addition of a pneumatic pumping system and fluid valves or a micro-PCR system and novel chemistries may be further included for enhancement of sensitivity.

The microchannel system enables a diffusion controlled binding event to occur either on the surface of a functionalized channel or on a functionalized fiber threaded in the middle of the channel for optimization of optical surface area. This allows an evanescent wave based sensor to detect analyte from fluid such as whole blood, by penetrating only about 1000 angstroms into the surface. Alternatively, in the case of the fiber imbedded in the middle of the stream, diffusion and separation can allow for an even simpler system in which readings can be taken on either sides of the fiber.

The fabrication of microfluidics in the inventive devices may be undertaken using technology from Micronics, Inc of Redmond, Wash. Specifically, thin film plastic laminate technology allows the creation of three dimensional microfluidic devices by laser cutting. Features are cut in plastic films and then subsequently layered together in the proper orientation to form a microfluidic network. Alternatively, the channels can be made in polydimethylsiloxane (PDMS), for example, using soft lithography techniques (Duffy et al., Anal Chem., 1998). Additionally, channels may directly be etched in silicon. Once the channels are fabricated, the bioactive agents may then be introduced to the device by immobilizing them to a glass surface. A glass surface may bonded to the channel forming the "cap" or top surface of the channel, such that the buffer stream comes in contact with the antibody laden surface. Alternatively, the glass surface is a glass optic fiber. The fiber optic may be either a single mode or preferably a multimode fiber. One or more fibers can be threaded through the center of the channel. In this case, the channel can be split into two blood streams surrounding a central buffer stream and diffusion would occur from both directions.

As opposed to cellular material and macromolecules, molecules such as the target analytes may pass across the blood/buffer fluid/fluid interface by diffusion. Because diffusion rate is inversely proportional to molecular size, a small molecule drug will migrate much farther than either blood-borne proteins or cells. This effectively creates a separation by size.

In one embodiment, the channel is designed such that only the drug molecules diffuse as far as the opposite wall of the microchannel (adjacent to the buffer stream). This wall constitutes a microarray as defined herein, as it may be coated with a predetermined amount of anti-drug antibodies that are pre-bound with fluorescently labeled drug molecules. An equilibrium exchange arises such that some of the labeled drug molecules are competitively displaced by the unlabeled drugs that have diffused to the wall (FIGS. 8, 19). The rate of exchange is concentration dependent, thus giving a measure of the concentration of drug in the blood. It is important to recognize that as an immunoassay, the forgoing may be adaptable to detect virtually any analyte for which an antibody can be generated.

In the foregoing embodiment, the interaction between the bioactive agent and analyte being detected, takes place on the buffer side of the channel, a fluorescence measurement can be done per TIRF spectrometer using a whole blood sample. As such, the fluorescence detection takes place on the buffer side of the channel and is not obscured by fluorescent moieties in the whole blood sample. Additionally, since the measurement is done in microchannels, only very small volumes of sample are needed.

In the preferred patch embodiment having a microarray of anti-glucose antibodies, glucose concentration may be measured in a sample of about 0.01 to about 0.4 µl preferably, about 0.05 to about 0.3 µl and most preferably 0.1 to 0.2 µl of blood. In another preferred patch embodiment having a microarray of anti-vancomycin antibodies, vancomycin concentration may be measured in a sample of about 0.01 to about 0.4 µl, preferably, about 0.05 to about 0.3 µl and most preferably 0.1 to 0.2 µl of blood. Additionally, in these embodiments, very rapid measurement of less than about a minute can be conducted.

In yet a further embodiment, the device monitors the concentration of an analyte and releases therapeutic agent in response to the analyte's concentration. Preferably, the analyte and is a particular drug or a metabolite of that drug and the therapeutic agent is the same drug. This configuration is particularly desirable when a drug has a narrow therapeutic range and it is important to maintain a certain concentration of the analyte/drug in the blood stream or at a particular site within the body. Accordingly, when the device detects a drop in concentration of the drug or one of its metablites in the blood stream or at a particular site within the body, the device can release a certain amount of the same drug to adjust the systemic or local drug concentration back to the desired level. For example, insulin or antibiotics such as vancomycin, maybe both the target analyte and the therapeutic agent.

The invention also contemplates a medical device capable of the localized delivery of one or more therapeutic agents upon detection of an analyte indicative of disease, i.e., a disease marker analyte. In another embodiment of this aspect of the invention, the device releases a single therapeutic agent in response to detection of several disease markers. Alternatively, the device may release different therapeutic agents appropriate for the detection of different disease markers. In another embodiment, drug is released through microneedles. In another embodiment, a therapeutic agent can be released into a saline solution compartment within the device which serves as a carrier fluid. In yet another embodiment of this aspect of the invention, liposomes are filled with a therapeutic agent and the liposomes are coated with antibodies specifically binding a specific cell-type. This method permits delivery of large amounts of drug to the appropriate cell type upon detection of a disease marker.

The device may contain one or more reservoirs comprising therapeutic agent(s). The reservoir holds therapeutic agent until it is directed by the biorecognition device upon detection of a disease marker, to release therapeutic agent in a controlled fashion, e.g., receives instruction as to release rate and quantity of agent to be released. Alternatively, a single release rate or dose may be programmed into the device. The reservoir can contain a mixture of one or more therapeutic agents. Alternatively, the device can comprise several reservoirs of one or more therapeutic agents. Preferably there are a plurality of reservoirs.

A "therapeutic agent," as used herein refers to compounds that are useful in or appropriate for treating a disease associated with a particular biological anomaly indicative of disease, e.g., disease marker analyte. Therapeutic agents of the invention are any therapeutic substance for the treatment of diseases including for example: pharmaceutical compounds that are preferably delivered locally such as chemotherapeutics, steroids, therapeutic nucleic acids including DNA, RNA, double stranded RNA (by means of RNA interface) and antisense RNA, or proteins such as immunoglobulins, growth factors, anti-inflammatory agents, or enzyme inhibitors, etc.

By release of therapeutic agent from the device, it may be preferable to establish an effective local concentration of the drug. For example in investigable and implantable embodiments of the device, the local concentration may substantially exceed the safe systemic concentration for the same drug, thus sparing the patient substantial discomfort yet maximizing efficacy. The localized release of corticosteroids appropriate for the treatment of localized inflammation is encompassed herein. Additionally, the localized release of pathogen-specific antibodies for the treatment of infection, is encompassed herein. The exact formulation and dosage can be chosen by the individual clinician in view of the patient's condition. (See e.g. Fingl et al., in The Pharmacological Basis of Therapeutics, 1975, Ch. 1 p. 1).

In another embodiment, a biological analyte indicative of unwanted cellular proliferation is detected and it is preferable to locally release therapeutic agent(s) that have an anti-proliferative effect. For example, sirolimus (rapamycin) or paclitaxel are very effective in inhibiting smooth muscle cell proliferation during neointimal hyperplasia.

In another example for responding to the presence of biological analytes indicative of unwanted proliferation, 5-FU-based chemotherapy comprises administration of 5-FU, its derivatives, alone or with other chemotherapeutics, such as leucovorin or with a DPD inhibitor such as uracil, 5-ethynyluracil, bromovinyluracil, thymine, benzyloxybenzyluracil (BBU) or 5-chloro-2,4-dihydroxypyridine, is released from the medical device. Furthermore, it has been found that co-administration of a 5'-deoxy-cytidine derivative of the formula (I) with 5-FU or a derivative thereof significantly improves delivery of a chemotherapeutic agent selectively to tumor tissues as compared with the combination of 5-FU or a derivative thereof with a DPD inhibitor 5-ethynyluracil.

Alternatively, genotoxic agents are those that form persistent genomic lesions and are preferred for use as chemotherapeutic agents in the clinical management of unwanted cellular proliferation. The rate of cellular repair of genotoxin-induced DNA damage, as well as the rate of cell growth via the cell division cycle, affects the outcome of genotoxin therapy. A general class of genotoxic compounds that are used for treating many cancers are DNA alkylating agents and DNA intercalating agents. Psoralens are genotoxic compounds known to be useful in the photochemotherapeutic treatment of cutaneous diseases such as psoriasis, vitiligo, fungal infections and cutaneous T cell lymphoma. Harrison's Principles of Internal Medicine, Part 2 Cardinal Manifestations of Disease, Ch. 60 (12th ed. 1991). Another general class of genotoxic compounds, members of which can alkylate or intercalate into DNA, includes synthetically and naturally sourced antibiotics. Of particular interest herein are antineoplastic antibiotics, which include but are not limited to the following classes of compounds represented by: amsacrine; actinomycin A, C, D (alternatively known as dactinomycin) or F (alternatively KS4); azaserine; bleomycin; caminomycin (carubicin), daunomycin (daunorubicin), or 14-hydroxydaunomycin (adriamycin or doxorubicin); mitomycin A, B or C; mitoxantrone; plicamycin (mithramycin); and the like. Still another general class of genotoxic agents that are commonly used and that alkylate DNA, are those that include the haloethylnitrosoureas, especially the chloroethylnitrosoureas. Representative members of this broad class include carmustine, chlorozotocin, fotemustine, lomustine, nimustine, ranimustine and streptozotocin. Haloethylnitrosourea first agents can be analogs or derivatives of any of the foregoing representative compounds.

Tumors currently manageable by platinum coordination compounds such as cisplatin or oxaliplatin include testicular, endometrial, cervical, gastric, squamous cell, adrenocortical and small cell lung carcinomas along with medulloblastomas and neuroblastomas. Other cytotoxic anti-cancer therapeutic agents include, for example, BEP (bleomycin, etoposide, cisplatin) for testicular cancer, MVAC (methotrexate, vinblastine, doxorubicin, cisplatin) for bladder cancer, MVP (mitomycin C, vinblastine, cisplatin) for non-small cell lung cancer treatment.

Yet another general class of genotoxic agents, members of which alkylate DNA, includes the sulfur and nitrogen mustards. These compounds damage DNA primarily by forming covalent adducts at the N7 atom of guanine. Representative members of this broad class include chlorambucil, cyclophosphamide, ifosfamide, melphalan, mechloroethamine, novembicin, trofosfamide and the like. Oligonucleotides or analogs thereof that interact covalently or noncovalently with specific sequences in the genome of selected cells can also be used as genotoxic agents, if it is desired to select one or more predefined genomic targets as the locus of a genomic lesion.

Another class of agents, members of which alkylate DNA, include the ethylenimines and methylmelamines. These classes include altretamine (hexamethylmelamine), triethylenephosphoramide (TEPA), triethylenethiophosphoramide (ThioTEPA) and triethylenemelamine, for example.

Additional classes of DNA alkylating agents include the alkyl sulfonates, represented by busulfan; the azinidines, represented by benzodepa; and others, represented by, e.g., mitoguazone, mitoxantrone and procarbazine. Each of these classes includes analogs and derivatives of the respective representative compounds.

Additional examples of cytotoxic therapeutic agents are antibodies complexing with a cell-specific antibody activates serum complement and/or mediate antibody-dependent cellular cytotoxicity. The antibodies which bind the cell can also be conjugated to a toxin (immunotoxins). The cytotoxic moiety of the immunotoxin may be a cytotoxic drug or an enzymatically active toxin of bacterial or plant origin, or an enzymatically active fragment of such a toxin. Enzymatically active toxins and fragments thereof used are diphtheria, non-binding active fragments of diphtheria toxin, exotoxin (from *Pseudomonas aeruginosa*), ricin, abrin, modeccin, alpha-sarcin, *Aleurites fordii* proteins, dianthin proteins, *Phytolacca americana* proteins (DAPI, PAPII, and PAP-S), *momordica charantia* inhibitor, curcin, crotin, sapaonaria officinalis inhibitor, gelonin, mitogellin, restrictocin, phenomycin, and enomycin. In another embodiment, the antibodies are conjugated to small molecule anticancer drugs. Conjugates of the monoclonal antibody and such cytotoxic moieties are made using a variety of bifunctional protein coupling agents. Examples of such reagents are SPDP, IT, bifunctional derivatives of imidoesters such a dimethyl adipimidate HCl, active esters such as disuccinimidyl suberate, aldehydes such as glutaraldehyde, bis-azido compounds such as bis (p-azidobenzoyl) hexanediamine, bis-diazonium derivatives such as bis-(p-diazoniumbenzoyl)-ethylenediamine, diisocyanates such as tolylene 2,6-diisocyanate, and bis-active fluorine compounds such as 1,5-difluoro-2,4-dinitrobenzene. The lysing portion of a toxin may be joined to the Fab fragment of the antibodies. Cytotoxic radiopharmaceuticals for treating cancer may be made by conjugating radioactive isotopes to the antibodies. The term "cytotoxic moiety" as used herein is intended to include such isotopes.

In one embodiment, therapeutic agents are inhibitors of receptor tyrosine kinases such as EGFR and HER2-neu and are employed as selective inhibitors of the growth of proliferative cells such as mammalian cancer cells. For example, erbstatin, an EGF receptor tyrosine kinase inhibitor, reduces the growth of EGFR expressing human carcinoma cells. Various derivatives of styrene are also stated to possess tyrosine kinase inhibitory properties and to be of use as anti-tumour agents. Two such styrene derivatives are Class I RTK inhibitors whose effectiveness have been demonstrated by attenuating the growth of human squamous cell carcinoma injected into nude mice. Certain 4-anilinoquinazoline derivatives are useful as inhibitors of receptor tyrosine kinases. The very tight structure-activity relationships shown by these compounds suggests a clearly-defined binding mode, where the quinazoline ring binds in the adenine pocket and the anilino ring binds in an adjacent, unique lipophilic pocket. Three 4-anilinoquinazoline analogues (two reversible and one irreversible inhibitor) have been evaluated clinically as anticancer drugs. Additionally, the monoclonal antibody trastazumab (Herceptin™) for the treatment of HER2-neu overexpressing metastatic breast cancers. Scheurle, et al., Anticancer Res 20:2091-2096, 2000.

In another embodiment, when a biological analyte indicative of a microbial pathogen is detected, it is preferable to locally release therapeutic agent(s) that have an antimicrobial effect. For example, it is preferable to release an antibiotic such as beta-Lactam Antibiotics, Aminoglycosides, Macrolides, Lincomycin, and Clindamycin Tetracyclines, Quinolones, Sulfonamides, Trimethoprim-Sulfamethoxazole and specifically: Amoxicillan, amoxicillian, Amoxicillin, ampicillin, Augmentin, Bactrim, BIAXIN, Ceclor, CEFTIN, Cipro, Clindamycin, Decadron, Diflucan, Doxycycline, erythromyacin, erythromycin, Erythromycin, flagyl, Floxin, Keflex, levoxil, macrobid, Metronizadole(Flagyl), Minocin, Minocyclin/Minocin, nizarol, norfloxacin, Nystatin, Penicillin, Polarol, Rocefin, Sulfa, Septra, Streptomycin, Tequinn, Tetracycline, tinnidazole, Valtrex, vibramcin, Zithromax, or zithromycin.

Upon detection of biological analytes indicative of viral infection, it is preferable to release antiviral compounds including protease inhibitors such as Invirase, Norvir, Viracept, Crixivan, or Frotovase, Saquinavir or other antivirals such as amantadine, rimantadine, zanamivir, oseltamivir, ribavirin, AZT, Didanosine, Zalcitabine, Stavudine, Lamivudine, Nevirapine, Delavirdine, Idoxuridine, Vidarabine, Trifluridine, Acyclovir, Famciclovir, Penciclovir, Valacyclovir, Ganciclovir, Foscarnet, Ribavirin, Amantadine and Rimantadine, Cidofovir, Interferons.

In another embodiment, when a biological analyte indicative of inflammation is detected, it is preferable to locally release therapeutic agent(s) that have an anti-inflammatory effect. Preferably such therapeutic agents are steroids such as prednisone/prednisolone, or non-steroidal an anti-inflammatory drugs (NSAIDs) such as Aspirin, Ibuprofen, Naproxen, Nabumetone, Celecoxib, Rofecoxib, or Valdecoxib. Such agents are particularly appropriate for the treatment of inflammation related diseases as Inflammatory Bowel Disease, Rheumatoid Arthritis and the like.

In another embodiment, when a biological analyte indicative of hyperglycemia is detected, it is preferable that the device release a therapeutic agent that will reduce serum glucose levels. For example, when excessively high levels of glucose are detected by the device, the device will responded by releasing a sufficient amount of insulin to bring the excessively high levels of glucose in the blood back to normal.

The invention envisages the medical device to have a plurality of microchips. Preferably, the microchips have the greatest currently available processing ability. Preferably, the plurality of microchips are all in communication with one another. Most preferably, the microchips are made of silicon germanium. Even more preferably, the microchips are International Business Machines (IBM)'s CMOS 9S low-k dielectric insulation high-performance chips to further provide for the highest efficiency, speed and power available in operating the medical device. The skilled artisan can readily appreciate that the device can have varying number of microchips because of the fact the devices listed below are capable of being embedded on a variable numbers of microchips.

Furthermore, each technological component of the device is optimized by the method in which it is uniquely integrated into this system. Recently, low-k dielectric insulation and silicon germanium technology has maximized microchip processing capabilities and efficiency. These chips are ideal for optical communication networks and by combining them with microarray bead technology, which conducts data by means of photo-optic signaling, the power behind both systems is optimized.

Another feature of the invention relates to a therapeutic agent releasing device capable of controlling release of therapeutic agent from a reservoir. For example, when the biometric recognition device determines the presence of a disease marker, the therapeutic agent releasing device is signaled to release therapeutic agent from a reservoir in a controlled fashion, i.e., it receives instruction as to release rate and/or quantity of drug to be released. In one embodiment, the therapeutic agent releasing device is a microchip located below microchips containing the device listed above and includes reservoirs for the controlled release of therapeutic agents. The substrate of the microchip contains the etched, molded, or machined reservoirs and serves as the support for the microchip. Any material that can serve as a support, is suitable for etching, molding, or machining, and is impermeable to the molecules to be delivered and to the surrounding fluids, for example, water, organic solvents, blood, electrolytes or other solutions, may be used as a substrate. Examples of substrate materials include ceramics, semiconductors, and degradable and non-degradable polymers. It is preferred that the substrate itself is non-toxic, sterile, and biocompatible. Nevertheless, toxic or otherwise non-biocompatible materials may be encapsulated in a biocompatible material, such as poly (ethylene glycol) or tetrafluoroethylene-like materials, before use. See U.S. Pat. No. 6,491,666 which is incorporated by reference in its entirety. A suitable therapeutic agent releasing device is available from MicroChips (Cambridge, Mass.). Preferably, the therapeutic agent releasing device has a plurality of reservoirs. In another embodiment of this aspect of the invention, the therapeutic agent releasing device signals the other devices or an external database as to the status of appropriate therapeutic agent release. In yet another embodiment, therapeutic agent release is in small doses serving as preliminary treatment while the therapeutic agent passes through additional microchips with independent wireless signaling systems which serve as checkpoints to ensure correct dosage prior to delivery.

Another feature of the invention relates to an interface device capable of facilitation communications between the microarray scanning device, the biorecognition device, and optionally, the therapeutic agent releasing device. Preferably, the interface device receives information regarding the presence; absence or quantity of an analyte from the biorecognition device and signals therapeutic agent releasing device to release a therapeutic agent or mixture of agents from one or more reservoirs. In one embodiment, the interface device has a wireless local area network (WLAN) transmitter and receiver. In particular see U.S. Pat. No. 5,832,296 or 6,542,717 which are hereby incorporated by reference in their entirety. In another embodiment the invention contemplates the use of a Personal Area Network (PAN) electrostatic communication to transmit signals between microchips and utilizes a therapeutic agent releasing device associated with reservoirs for therapeutic agent release in order to deliver drugs into the body upon receiving respective signals from the analysis in the biorecognition device. Preferably, in implantable and ingestible embodiments, two bordering PAN transmitters are located underneath the microarray—one bordering the microarray scanning device and the other bordering the therapeutic agent releasing device controlling the reservoir below. PAN transmitters signal for release of therapeutic agent as specified by array results. Appropriate hardware may be obtained from Interval Research Corp., Palo Alto, Calif. and PAN transmitters from International Business Machines Corp., Armonk, N.Y.

In another embodiment of this aspect of the invention, the plurality of microchips transmit their information to external sources such as a hand held monitoring device or computers at network headquarters operated by wireless data communications systems. In a further embodiment, where the device is a patch for treating diabetes, the patch measures insulin levels and communicates with a second device measuring carbohydrate levels or third device measuring sweat glands or arithmic levels. A process control decision through a comparison of the interactions between analytes and the different devices and the database of physical parameter data will determine whether a release an amount of glucose or insulin is appropriate, forming a closed loop system which accounts for other factors imperative in determining glucose/insulin release.

In one embodiment the invention has an energy source to power the medical device. For example, the device is powered by a battery. In another embodiment, the power source is provided by a Personal Area Network.

Applications of this invention range from military to commercial use. For instance, the device could be used by civilians in nations afflicted by viruses such as SARS where real-time diagnosis acquires a substantial importance. With the rise of bioterrorism methods of detecting pathogens are of increasing value to defense departments worldwide. Likewise, the invention could be used to detect bacterial infections or other gut-related diseases and to deliver an immediate real time diagnosis of protein activity as it travels through the intestinal system seeing as the gut is one of the largest centers for the growth of infectious diseases. Likewise, applications of protein microarray technology which are currently limited by problems such as isolating high affinity and specificity protein ligands or BSA obscuring peptides of interest on aldehyde slides could be maximized by using selective protein arrays in vivo and dispensing antibodies or drugs corresponding to targeted protein classes. Additionally, the inventive devices could be particularly useful for clinical trial research purposes for efficient monitoring the levels and effects of experimental drugs to develop pharmacokinetic models.

Indeed, there could be commercial, medical, research/educational, and military and community service/humanitarian applications of this device.

EXAMPLES

Example 1

Fiber-Optic Total Internal Reflection Fluorescence Biosensor Specifications

Figure 12:
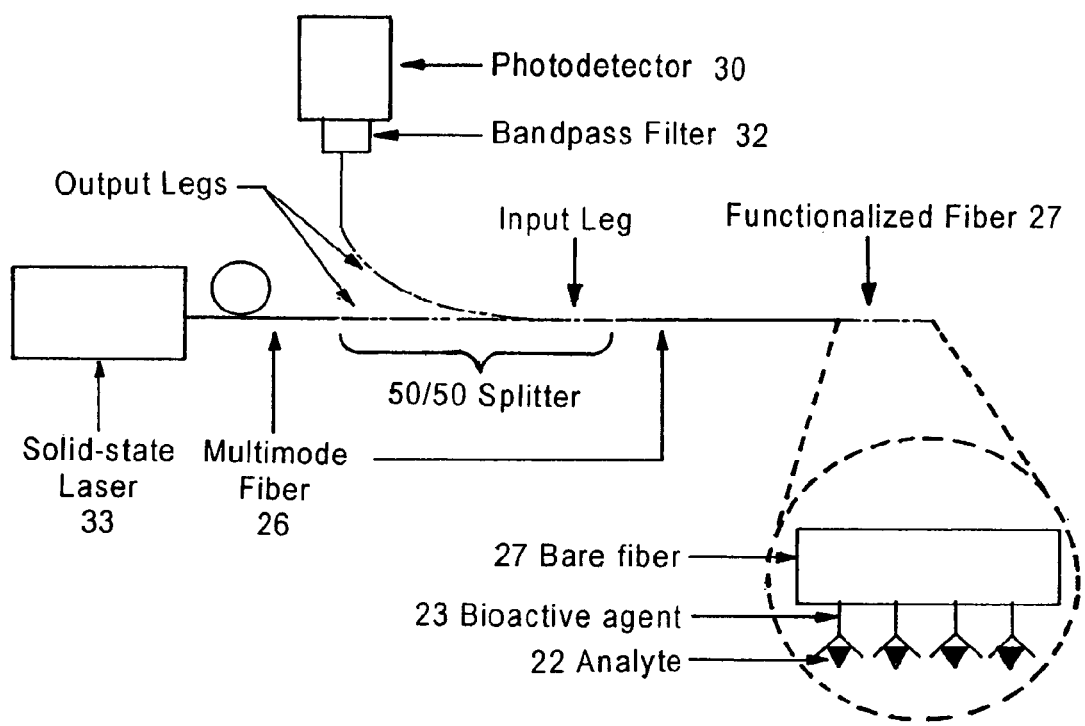
FIG. 12. Illustrates an exemplary portion of a microarray and microarray scanning device utilizing a TIRF sensor. Incoming laser light from a laser 33 is directed through a multimode fiber 26 and the output leg of a 50:50 fiber optic splitter 31 onto the functionalized unclad fiber 27. In the case of one assay the fluorophore-labeled analyte displaced from the bioactive agent by a competitive binding process resulting from the presence of analyte in the bodily fluid, and as a result the photonic energy coupled into the fiber at the evanescent wave is reduced. This reduction in light intensity is detected by the photo diode and associated amplifier. Emitted fluorescence characteristic of the interaction between an analyte 22 and a bioactive agent 23 couples back into the fiber and propagates towards the detector 30 with little interference from the laser light. A laser coupled to a fiber provides light at 660 nm. In one example, the system works with either a 200 µm core functionalized fiber and splitter or a 62.5 µm core functionalized fiber and splitter. The fiber core diameter is the same for the entire system. In either a 62.5 or 200 µm core system, higher order modes of the fiber (the edges of the core) are excited to both maximize the evanescent wave energy and make the 1×2 coupler perform more uniformly. This is different based on the fiber core diameter.

A fiber-optic total internal reflection fluorescence (TIRF) biosensor was constructed and constitutes a microarray and microarray scanning device as defined in this specification. See Preininger et al. (*Analytica Chimica Acta*, 2000, 403, 67-76). The laser light is directed from the laser light source to the flow cell to the detector all via a series of optical fibers. A schematic of this fiber optic based unit is shown in FIG. 12. In the sensor, incoming laser light is directed through the output leg of a 50:50 fiber optic splitter onto the functionalized fiber. Emitted fluorescence couples back into the fiber and propagates towards the detector with little interference from the laser light. This design has several advantages: The start-to-finish use of the fibers eliminates losses due to free space coupling; the fibers are robust transporters of light and thus are insensitive to vibration and multiple fibers can readily be joined together by commercially available fiber optic connectors. Therefore, a microarray can be either the functionalized surface of one fiber or the functionalized surfaces of a plurality of fibers.

Figure 13:
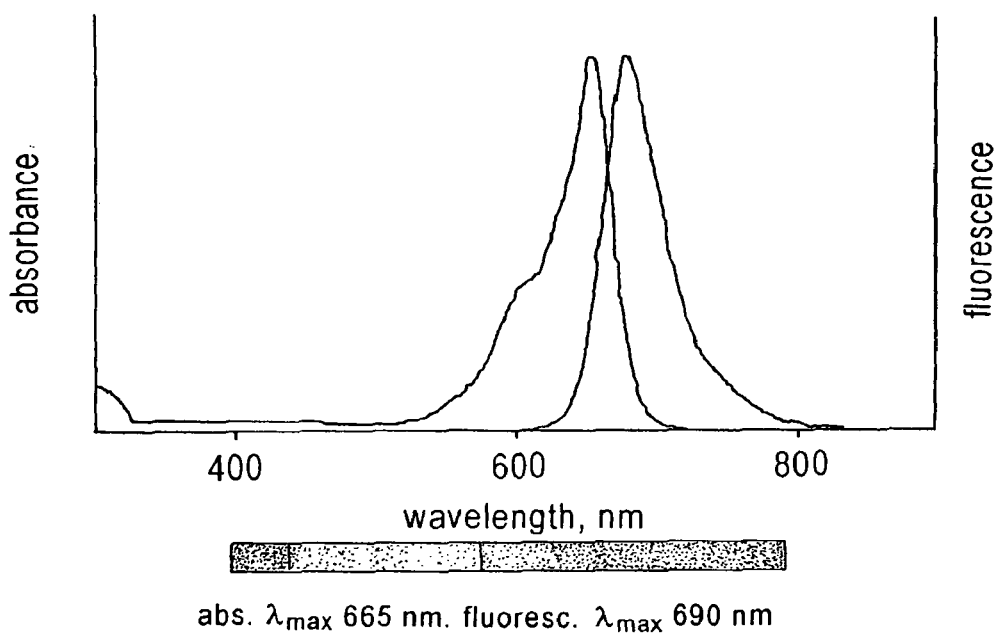
FIG. 13. Illustrates the fluorescence and absorbance of the Atto 655 fluorophore.

The expected output fluorescence intensity delivered to the photodiode as a function of input laser power and fiber characteristics of the Atto 655 fluorophore (see FIG. 13), using the methodology described in Celebre et al. (*Measurement Science and Technology*, 1992, 3, 1166-1173) are shown in Table 1 with the following system parameters:

a surface concentration of ~200 ng/cm$^2$ [Tedeschi et al., *Biosensors and Bioelectronics*, 2003, 19(2), 85-93]

the fluorophore Atto 655 (Sigma Aldrich) with spectral characteristics QY=0.3∈=110,000

TABLE 1

Fluorescence output as a function of laser power and fiber characteristics.

| Fiber Length (cm) | Input Laser Power (mW) | Fiber Diameter (μm) | Output Power (pW) |
|---|---|---|---|
| 1 | 0.5 | 62.5 | 82 |
| 1 | 0.5 | 200 | 163 |
| 1 | 1.0 | 62.5 | 163 |
| 1 | 1.0 | 200 | 327 |
| 1 | 3.0 | 62.5 | 489 |
| 1 | 3.0 | 62.5 | 489 |
| 1 | 3.0 | 200 | 980 |
| 1 | 3.0 | 200 | 980 |
| 1 | 5.0 | 62.5 | 815 |
| 1 | 5.0 | 200 | 1,630 |
| 3 | 0.5 | 62.5 | 244 |
| 3 | 0.5 | 200 | 490 |
| 3 | 3.0 | 62.5 | 1,470 |
| 3 | 3.0 | 200 | 2,940 |
| 5 | 0.5 | 62.5 | 407 |
| 5 | 0.5 | 200 | 817 |
| 5 | 3.0 | 62.5 | 2,440 |
| 5 | 3.0 | 200 | 4,900 |

A typical photodiode (e.g. Pacific Sensor part 1-6-T052S1) accurately measures signals in the picowatt range. It is clear that even with a conservative estimate of 50% losses in the system, the parameters of the biosensor can be adjusted such that the output power is two orders of magnitude greater than the sensitivity floor of the detector.

Example 2

Integrated Patch System

The exemplary patch device represents a painless method of automatically drawing and sampling 0.1 ml of blood for vancomycin. Each patch consists of two parts, a disposable portion (Assay Device) that contains the single use microneedles and micro channel, and a reusable part that contains the remaining optics, electronics and mechanics (Assay Reader Device). FIGS. 5, 7

Micro-needles automatically draw small quantities of blood painlessly. A mechanical actuator inserts and withdraws the needle. The inventive devices makes several measurements after the patch is applied. However, each micro-needle is only used once to avoid clotting. The requirement for multiple blood draws calls for a mechanical actuator that can not only insert and withdraw the needle but also dispose the used needle and reload a new needle. The micro needles are sharp, robust and minute enough to penetrate the outer layer of the skin in a completely painless manner. Their design contributes to the low-cost, disposable, self-employed, biocompatible nature of the device.

Needles are produced photolithographically in molds at SNF. Microchannels on the "top" assay device portion of the patch device contain laminar flow and reservoir elements, along with the necessary structures to capture the fiber sensor. Two separate fluid flow elements operate of the patch—blood flow through the needle into a reservoir and blood/buffer flow through the channel. FIG. 5. The following table shows the design specifications for the channel.

TABLE 2

|  | Blood Cells | Blood Proteins | Vancomycin |
|---|---|---|---|
| Hydrodynamic Size | ~5 μm | ~8 nm | ~1 nm |
| Diffusion Coefficient (cm$^2$/s) | ~1 × 10$^{-9}$ | ~1 × 10$^{-6}$ | 1 × 10$^{-5}$ |
| Diffusion Distance (μm) | ~1 | ~32 | ~100 |

| | |
|---|---|
| Length | 1 cm |
| Height | 100 μm |
| Thickness | 25 μm |
| Stripe Height | 50 μm |
| Cross Sec. Area | 2500 μm$^2$ |
| Stripe Cross Sec. Area | 1250 μm$^2$ |
| Channel Volume | 0.125 μl |
| Flow Rate | 0.15 μl/min |
| Total Sample Size | 0.1 μl |
| Flow Velocity | 0.1 cm/s |
| Diffusion Time | 10 s |
| Viscosity of Buffer | 0.01 cm$^2$/s |
| Reynolds Number | 0.11 |

The non-disposable component (Assay Reader Device) of the patch contains 12 single use disposable components (Assay Devices) which will be mounted on it. FIG. 7. Custom microfluidics fabrication is obtained from Micronics. Specifications are as follows:

Specifications

| | Item | Specifications |
|---|---|---|
| 1 | Sample Loading | Whole blood, 100 nl |
| 2 | Functionalized surface (microarray) | Glass surface immobilized with fluorescent sensor molecules<br>Prepared after card fabrication by Client |
| 3 | Reagents | Buffer (Phosphate buffer saline), 1-2 μl |
| 4 | Fluid actuation | Active pumping |
| 5 | Sensing channel | Capped on one side by functionalized surface<br>Channel is about 100 μm deep orthogonal from functionalized surface<br>Channel length is about 1 cm |
| 6 | Detection | Fluorescent measurements (photomultiplier or equivalent detector). |
| 7 | Time of Assay | Less than 2 minutes |
| 8 | User Interface to device | WLAN |
| 9 | Card Materials | low auto-fluorescent 1 |

The optical sensor microarray scanning device provides an electronic signal to a biorecognition device based on the fluorescence of the interaction between bioactive agent and analyte excited by an evanescent wave produced by the laser. The optical sensor frequency is determined based on a cost tradeoff between laser, PIN diode, and fluorescent molecule costs.

The non-disposable evanescent sensor fiber (microarray scanning device within the Assay Reader Device) is attached to the disposable blood draw fluidics subsystem (containing the microarray in the Assay Device) to create a complete single use assay device. The assay device is packaged in groups of 6 and 12 per assay reader device.

Figure 14:
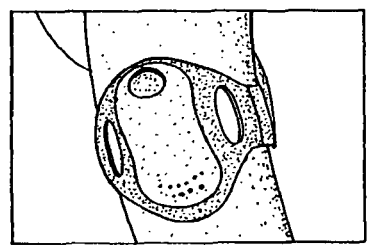
FIG. 14. An image of a model assay reader device worn on the human arm.
Figure 15:
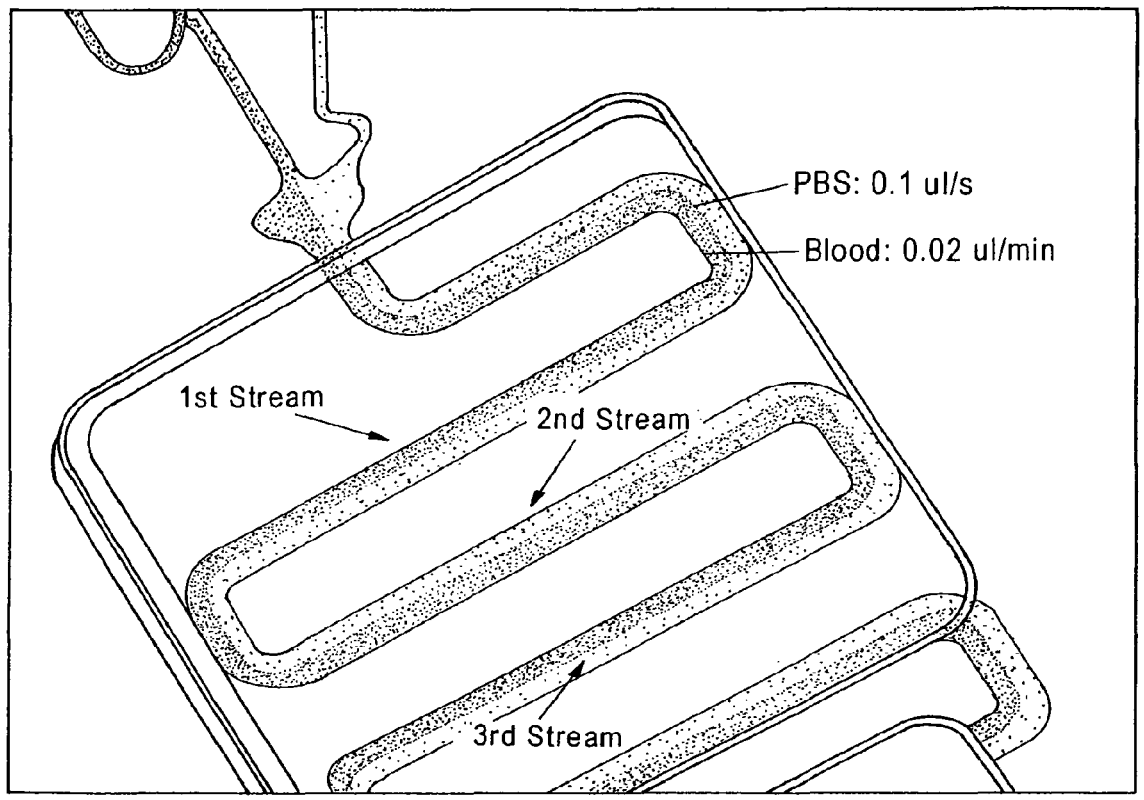
FIG. 15. Is an image of a two the convergence in a microchannel of a stream of PBS flowing at 0.1 µl/s and a stream of blood at 0.02 µl/min. Visually, there is little mixing between the streams at the diffusional interface. However, molecules with higher diffusional coefficients will traverse the diffusional interface.
Figure 16:
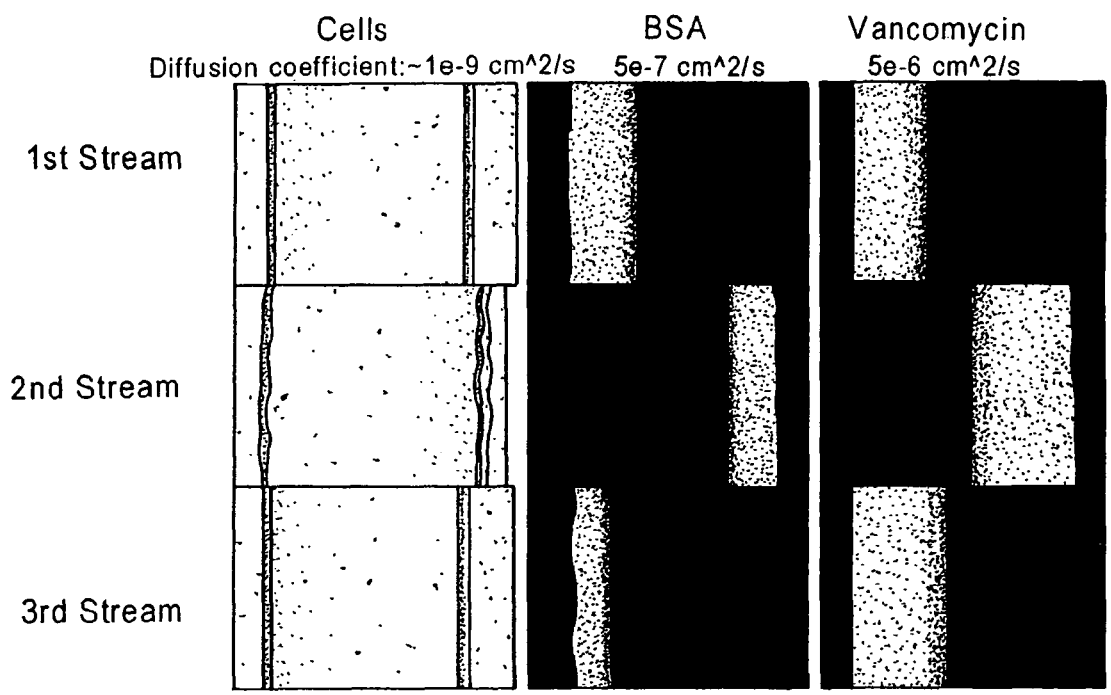
FIG. 16. Is an image of the diffusional coefficients of cells, bovine serum albumin and vancomycin.
Figure 17A:
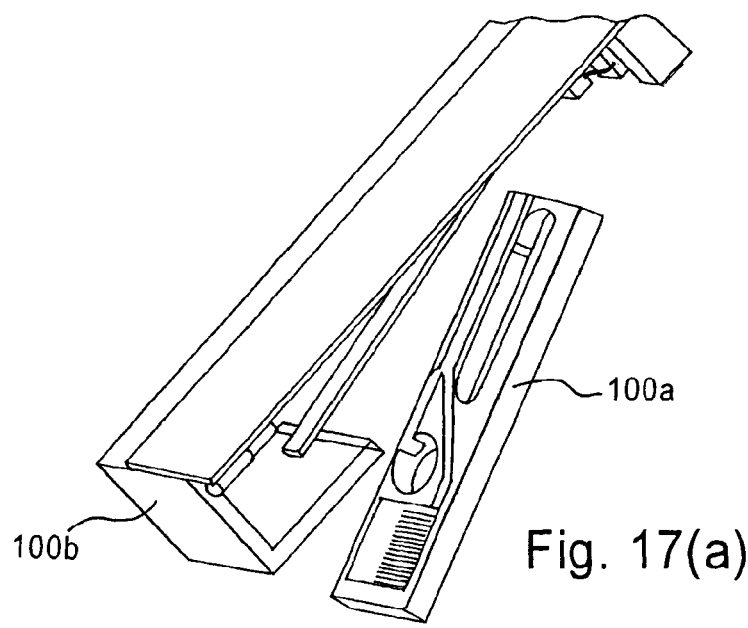
FIG. 17. Is an illustration of an exemplary device of the invention. A) The figure shows that the device may be separable in two components: A disposable layer having microneedles, microchannels and a microarray 100a and a non-disposable portion 100b in optical communication with the disposable portion having the microarray scanning device and other electronics. B) The disposable portion 100a of the patch contains a reservoir 13 into which a blood is pumped from the microneedles, a second reservoir containing a buffer 14 and common microchannel for laminar flow 15 which is the confluence of a buffer 15a and a blood inlet 15b, as well as a receptacle for waste 16. Additionally, the uncladed portion of a fiber optic comprising the microarray is shown 26. C) shows several disposable and non-disposable portions together.
Figure 17B:
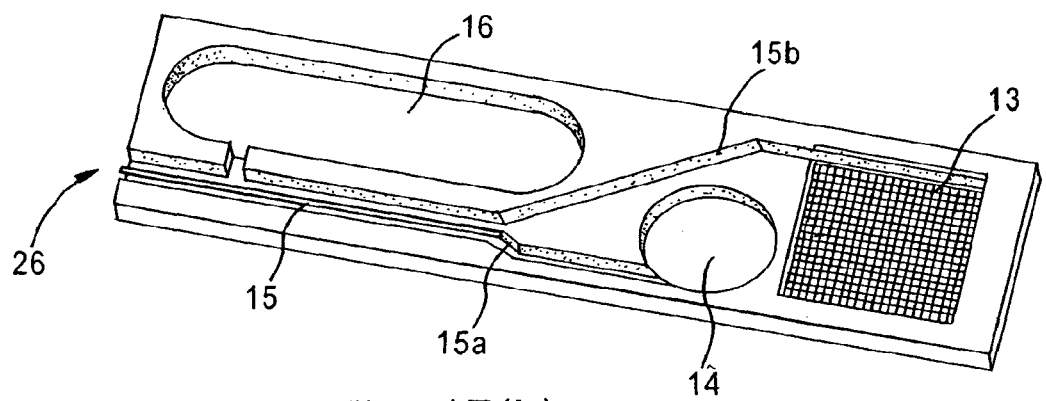
Figure 17C:
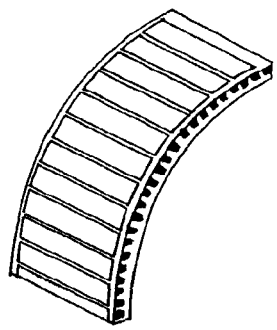

For testing the maximum size of an integrated system is similar to the body media device which is show in FIG. 14.

Blood flows through the micro needles into the blood reservoir. The buffer and blood form a laminar flow through the channel (FIG. 5; shown in black). A 660 nm laser excites fluorophore, which are bound to the surface of the fiber (in gray). Drugs in blood displace the labeled drugs on the fiber, and the intensity of the fluorescence is decreased. A sensor on the end of the fiber in the Reader detects a reduction in signal level. This reduction is reported to the biometric recognition device's associated database.

The devices are formed into a comb like structure; the 12-unit assay model is shown in FIG. 7. In the figures the control electronics are mounted in the top portion of the device (assay reader device). The actuation mechanisms are in the bottom of the device (assay device).

The end view of the reader shows the cavity for the assay device in the bottom of the reader. An optical and mechanical interface exists between the two components.

Along the top of the cavity are 12 springs which are used to force the micro needles into the skin. Also there is a solenoid that releases the spring. Each spring presses on the top of one of the 12 disposable components.

One end of each of the assay device fingers forms a hinge within the assay device, so the spring forces the assay device down through a layer of film, which covers the bottom of the assay device.

The optical fiber passes over the hinge and terminates at an optical splitter, which is mounted on the bottom of the electronics printed circuit board. The interface between the assay device and the assay reader device is a small air gap.

Figure 6:
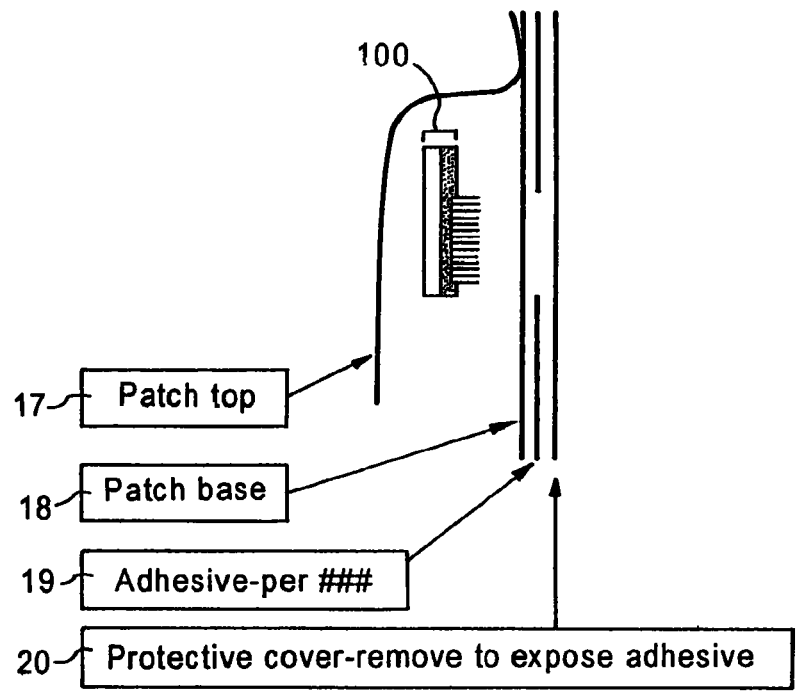
FIG. 6. Illustrates how the patch 100 may be packaged prior to application to a patient. The patch may be covered with a protective layer 17 and have a patch base 18 through with the microneedles will penetrate upon application. The base 18 provides the added benefit of maintaining sterility of the microneedles prior to application. An adhesive 19 serves to fasten the patch to the skin of the subject. Additionally, a protective cover 20 is provided which is removed to expose the adhesive layer 19.

This end view of one of the 12 assay device fingers shows the package. The assay device is inside a sterile patch package. Under the micro needles there is a portion of the patch that is designed to allow the needles to penetrate and enter skin. The patch is held in place with an adhesive as shown in FIG. 6. Finally there is a protective cover. The top of the patch is designed to allow insertion into the reader. The optical signal passes through a portion of this seal between the end of the fiber and the splitter.

In this disclosure there is described only the preferred embodiments of the invention and but a few examples of its versatility. It is to be understood that the invention is capable of use in various other combinations and environments and is capable of changes or modifications within the scope of the inventive concept as expressed herein. Thus, for example, those skilled in the art will recognize, or be able to ascertain, using no more than routine experimentation, numerous equivalents to the specific substances and procedures described herein. Such equivalents are considered to be within the scope of this invention, and are covered by the following claims.

What is claimed is:

1. A method of detecting an interaction if of an ingestible medical device with a gastric fluid comprising:
    administering an ingestible medical device to a subject, wherein the ingestible medical device comprises:
        a microchip enclosed in said ingestible medical device, wherein said device is configured to interact with the gastric fluid when ingested by the subject;
        said microchip comprising an interface device that is configured to wirelessly transmit to an external device located outside the subject a signal that is generated upon interaction of the device with the gastric fluid,
        a biocompatible coating covering at least a portion of the device, wherein a) a portion of the coating is characterized by interconnected pores of sufficient size to allow for flow of bodily fluids into the ingestible medical device and b) another portion of the coating covering a larger portion of device that is not porous;
    operating the ingestible medical device to transmit the signal upon interaction of the device with the gastric fluid.

2. The method of claim 1 further comprising releasing a therapeutic agent to the subject.

3. The method of claim 1 wherein the external device comprises a biometric recognition device that analyzes the signal and determines the absence, presence, or quantity of an analyte where the device interacts with the gastric fluid.

4. The method of claim 3 wherein the biometric recognition device matches data provided by the signal to a known analyte interaction profile to determine the presence, absence, or quantity of the analyte.

5. The method of claim 3 wherein the biometric recognition device is worn on the skin as a patch.

6. The method of claim 1 wherein the signal is generated based upon natural electric currents in the body.

7. The method of claim 1 wherein said signal is indicative of bio-electric, bio-magnetic, or biochemical characteristics of the device's interaction with the gastric fluid.

8. The method of claim 1 further comprising measuring a physiological condition of the subject.

9. The method of claim 8 wherein the interface device is configured to transmit one or more physiological conditions.

10. The method of claim 2 wherein releasing the therapeutic agent releasing comprises release from one or more reservoirs of therapeutic agent of the ingestible medical device.

11. The method of claim 10 wherein releasing the therapeutic agent signals the external device of the status of therapeutic agent release.

12. The method of claim 1 wherein the external device is a computer.

13. The method of claim 1 wherein the external device is in communication with an external network.

14. The method of claim 1 comprises using a personal area network for the ingestible medical device to communicate with the external device.

* * * * *